(12) United States Patent
Drasler et al.

(10) Patent No.: US 8,900,264 B2
(45) Date of Patent: Dec. 2, 2014

(54) VALVULOPLASTY CATHETER AND METHODS

(75) Inventors: William Drasler, Minnetonka, MN (US); Wes Pedersen, Minneapolis, MN (US); Mark Ungs, Minnetonka, MI (US)

(73) Assignee: InterValve, Inc., Plymouth, MN (US)

( * ) Notice: Subject to any disclaimer, the term of this patent is extended or adjusted under 35 U.S.C. 154(b) by 387 days.

(21) Appl. No.: 13/108,938

(22) Filed: May 16, 2011

(65) Prior Publication Data

US 2011/0218564 A1 Sep. 8, 2011

Related U.S. Application Data

(63) Continuation of application No. 12/576,970, filed on Oct. 9, 2009, now Pat. No. 7,951,111.

(60) Provisional application No. 61/104,636, filed on Oct. 10, 2008, provisional application No. 61/112,566, filed on Nov. 7, 2008, provisional application No. 61/145,705, filed on Jan. 19, 2009.

(51) Int. Cl.
| | |
|---|---|
| *A61M 29/00* | (2006.01) |
| *A61M 29/02* | (2006.01) |
| *A61M 37/00* | (2006.01) |
| *A61M 31/00* | (2006.01) |
| *A61M 25/10* | (2013.01) |
| *A61B 17/22* | (2006.01) |
| *A61M 25/00* | (2006.01) |

(52) U.S. Cl.
CPC ... *A61M 25/1002* (2013.01); *A61M 2025/1047* (2013.01); *A61M 25/1018* (2013.01); *A61M 29/02* (2013.01); *A61M 25/1029* (2013.01); *A61M 2025/1086* (2013.01); *A61M 2025/1088* (2013.01); *A61M 25/1011* (2013.01); *A61B 17/22012* (2013.01); *A61M 2025/1031* (2013.01); *A61M 2025/0002* (2013.01); *A61B 2017/22098* (2013.01); *A61M 2025/1075* (2013.01)
USPC ............... 606/194; 604/500; 604/103.07

(58) Field of Classification Search
USPC .................................. 604/509; 606/193, 194
See application file for complete search history.

(56) References Cited

U.S. PATENT DOCUMENTS 4,137,922 A * 2/1979 Leininger et al. ............. 606/193
4,327,736 A   5/1982 Inoue (Continued)

FOREIGN PATENT DOCUMENTS

| EP | 0344530 A1 | 12/1989 |
|---|---|---|
| EP | 0351734 A1 | 1/1990 |

(Continued)

OTHER PUBLICATIONS

United States Patent and Trademark Office, Notice of Allowance mailed Jan. 24, 2011 in U.S. Appl. No. 12/576,970, 10 pages.

(Continued)

*Primary Examiner* — Quynh-Nhu H Vu
*Assistant Examiner* — Jenna Zhang
(74) *Attorney, Agent, or Firm* — Inskeep IP Group, Inc

(57) ABSTRACT

A valvuloplasty catheter has a dog-bone shaped balloon with semi-compliant smaller diameter waist and non-compliant larger diameter bulbous end regions. The balloon centers across the valve with the waist adjacent to the annulus. One bulbous region serves to hyperextend the valve leaflets and the other assists in stabilizing the balloon position to reduce migration. The semi-compliant waist increases in diameter as fluid enters the balloon until it comes into contact with the valve annulus. The pressure within the balloon per unit of volume delivery has a greater slope after contact with the annulus than before resulting in a change in slope for the pressure versus volume curve. The diameter of the balloon and annulus are determined at this inflection point when the balloon contacts the annulus.

22 Claims, 19 Drawing Sheets

(56) References Cited

U.S. PATENT DOCUMENTS

| | | | |
|---|---|---|---|
| 4,328,811 A | 5/1982 | Fogarty | |
| 4,572,186 A | 2/1986 | Gould et al. | |
| 4,630,609 A | 12/1986 | Chin | |
| 4,723,549 A | 2/1988 | Wholey et al. | |
| 4,763,654 A | 8/1988 | Jang | |
| 4,777,951 A | 10/1988 | Cribier et al. | |
| 4,787,388 A | 11/1988 | Hofmann | |
| 4,796,629 A | 1/1989 | Grayzel | |
| 4,819,751 A | 4/1989 | Shimada et al. | |
| 4,878,495 A | 11/1989 | Grayzel | |
| 4,906,244 A | 3/1990 | Pinchuk et al. | |
| 4,909,252 A | 3/1990 | Goldberger | |
| 4,927,412 A | 5/1990 | Menasche | |
| 4,938,676 A | 7/1990 | Jackowski et al. | |
| 4,986,830 A | 1/1991 | Owens et al. | |
| 5,017,325 A | 5/1991 | Jackowski et al. | |
| 5,037,392 A | 8/1991 | Hillstead | |
| 5,055,024 A | 10/1991 | Jackowski et al. | |
| 5,074,845 A | 12/1991 | Miraki et al. | |
| 5,108,415 A | 4/1992 | Pinchuk et al. | |
| 5,156,612 A | 10/1992 | Pinchuk et al. | |
| 5,171,299 A | 12/1992 | Heitzmann et al. | |
| 5,223,205 A | 6/1993 | Jackowski et al. | |
| 5,236,659 A | 8/1993 | Pinchuk et al. | |
| 5,250,070 A | 10/1993 | Parodi | |
| 5,275,169 A | 1/1994 | Afromowitz et al. | |
| 5,295,958 A | 3/1994 | Shturman | |
| 5,295,995 A | 3/1994 | Kleiman | |
| 5,304,197 A | 4/1994 | Pinchuk et al. | |
| 5,330,429 A | 7/1994 | Noguchi et al. | |
| 5,342,305 A | 8/1994 | Shonk | |
| 5,352,199 A * | 10/1994 | Tower | 604/103.07 |
| 5,356,591 A | 10/1994 | Pinchuk et al. | |
| 5,443,446 A | 8/1995 | Shturman | |
| 5,447,497 A | 9/1995 | Sogard et al. | |
| 5,449,371 A | 9/1995 | Pinchuk et al. | |
| 5,453,091 A | 9/1995 | Taylor et al. | |
| 5,470,313 A * | 11/1995 | Crocker et al. | 604/103.07 |
| 5,484,411 A | 1/1996 | Inderbitzen et al. | |
| 5,501,667 A | 3/1996 | Verduin, Jr. | |
| 5,545,209 A | 8/1996 | Roberts et al. | |
| 5,549,551 A | 8/1996 | Peacock, III et al. | |
| 5,647,847 A | 7/1997 | Lafontaine et al. | |
| 5,653,690 A | 8/1997 | Booth et al. | |
| 5,693,014 A | 12/1997 | Abele et al. | |
| 5,728,064 A | 3/1998 | Burns et al. | |
| 5,738,653 A | 4/1998 | Pinchuk et al. | |
| 5,752,522 A | 5/1998 | Murphy | |
| 5,792,300 A | 8/1998 | Inderbitzen et al. | |
| 5,795,325 A * | 8/1998 | Valley et al. | 604/509 |
| 5,797,877 A | 8/1998 | Hamilton et al. | |
| 5,843,116 A | 12/1998 | Crocker et al. | |
| 5,868,708 A | 2/1999 | Hart et al. | |
| 5,902,308 A | 5/1999 | Murphy | |
| 5,908,448 A | 6/1999 | Roberts et al. | |
| 5,947,924 A | 9/1999 | Liprie | |
| 5,961,536 A | 10/1999 | Mickley et al. | |
| 6,010,480 A | 1/2000 | Abele et al. | |
| 6,010,511 A | 1/2000 | Murphy | |
| 6,110,142 A | 8/2000 | Pinchuk et al. | |
| 6,136,258 A | 10/2000 | Wang et al. | |
| 6,190,354 B1 | 2/2001 | Sell et al. | |
| 6,210,338 B1 | 4/2001 | Afremov et al. | |
| 6,241,678 B1 | 6/2001 | Afremov et al. | |
| 6,267,747 B1 | 7/2001 | Samson et al. | |
| 6,296,660 B1 | 10/2001 | Roberts et al. | |
| 6,344,045 B1 | 2/2002 | Lim et al. | |
| 6,409,741 B1 | 6/2002 | Crocker et al. | |
| 6,416,494 B1 | 7/2002 | Wilkins | |
| 6,495,090 B1 | 12/2002 | Wilkins | |
| 6,500,146 B1 | 12/2002 | Pinchuk et al. | |
| 6,500,148 B1 | 12/2002 | Pinchuk et al. | |
| 6,511,469 B2 | 1/2003 | Ackerman et al. | |
| 6,537,247 B2 | 3/2003 | Shannon | |
| 6,544,224 B1 | 4/2003 | Steese-Bradley | |
| 6,562,056 B2 | 5/2003 | Jervis | |
| 6,565,589 B1 | 5/2003 | Jervis et al. | |
| 6,607,544 B1 | 8/2003 | Boucher et al. | |
| 6,607,545 B2 | 8/2003 | Kammerer et al. | |
| 6,626,861 B1 | 9/2003 | Hart et al. | |
| 6,632,196 B1 | 10/2003 | Houser | |
| 6,645,222 B1 | 11/2003 | Parodi et al. | |
| 6,663,647 B2 | 12/2003 | Reiley et al. | |
| 6,733,513 B2 | 5/2004 | Boyle et al. | |
| 6,896,842 B1 | 5/2005 | Hamilton et al. | |
| 6,942,680 B2 | 9/2005 | Grayzel et al. | |
| 7,229,403 B2 | 6/2007 | Schock et al. | |
| 7,309,324 B2 | 12/2007 | Hayes et al. | |
| 7,354,419 B2 | 4/2008 | Davies, Jr. et al. | |
| 7,618,432 B2 | 11/2009 | Pedersen et al. | |
| 7,744,620 B2 | 6/2010 | Pedersen et al. | |
| 2001/0047163 A1 | 11/2001 | Samson et al. | |
| 2003/0028211 A1 | 2/2003 | Crocker et al. | |
| 2004/0073164 A1 | 4/2004 | Boatman et al. | |
| 2004/0093008 A1 | 5/2004 | Zamore | |
| 2005/0059965 A1 * | 3/2005 | Eberl et al. | 604/103.07 |
| 2005/0075662 A1 | 4/2005 | Pedersen et al. | |
| 2005/0090846 A1 * | 4/2005 | Pedersen et al. | 606/159 |
| 2005/0137621 A1 | 6/2005 | Stahl et al. | |
| 2006/0015133 A1 | 1/2006 | Grayzel et al. | |
| 2006/0016064 A1 | 1/2006 | Boatman et al. | |
| 2006/0085024 A1 | 4/2006 | Pepper et al. | |
| 2007/0142771 A1 | 6/2007 | Durcan | |
| 2007/0213663 A1 | 9/2007 | Wang | |
| 2007/0213760 A1 | 9/2007 | Hayes et al. | |
| 2007/0219490 A1 | 9/2007 | Pepper et al. | |
| 2008/0009746 A1 | 1/2008 | Forster et al. | |
| 2008/0015687 A1 | 1/2008 | Lashinski et al. | |
| 2010/0228277 A1 | 9/2010 | Pedersen et al. | |

FOREIGN PATENT DOCUMENTS

| | | |
|---|---|---|
| EP | 0419291 A1 | 3/1991 |
| EP | 0669143 A1 | 8/1995 |
| EP | 0829271 A2 | 3/1998 |
| EP | 1062966 A1 | 12/2000 |
| EP | 1352671 A1 | 10/2003 |
| EP | 1352672 A2 | 10/2003 |
| WO | WO89/02763 A1 | 4/1989 |
| WO | WO91/01773 A1 | 2/1991 |
| WO | WO95/23625 A1 | 9/1995 |
| WO | WO99/15223 A1 | 4/1999 |

OTHER PUBLICATIONS

United States Patent and Trademark Office, Final Office Action mailed Oct. 18, 2010 in U.S. Appl. No. 12/576,970, 25 pages.

United States Patent and Trademark Office, Office Action mailed May 28, 2010 in U.S. Appl. No. 12/576,970, 20 pages.

WIPO, U.S. International Search Authority, International Search Report mailed Feb. 5, 2010 in International Patent Application No. PCT/US2009/060239, 3 pages.

Eisenhauer, A.C., et al., "Balloon aortic valvuloplasty revisited: the role of the inoue balloon and transseptal antegrade approach," *Catheter Cardiovasc Interv.* Aug. 2000;50(4):484-91.

United States Patent and Trademark Office, Office Action mailed Mar. 16, 2012 in U.S. Appl. No. 12/783,438, 11 pages.

* cited by examiner

VALVULOPLASTY CATHETER AND METHODS

RELATED APPLICATIONS

The present application is a continuation of U.S. patent application Ser. No. 12/576,970 filed Oct. 9, 2009 entitled Valvuloplasty Catheter and Methods, issuing on May 31, 2011 as U.S. Pat. No. 7,951,111, which claims priority to U.S. Provisional Application Ser. No. 61/104,636 filed Oct. 10, 2008 entitled Valvuloplasty Catheter And Methods, U.S. Provisional Application Ser. No. 61/112,566 filed Nov. 7, 2008 entitled Valvuloplasty Catheter And Methods, and U.S. Provisional Application Ser. No. 61/145,705 filed Jan. 19, 2009 entitled Valvuloplasty Catheter And Methods, all of which are hereby incorporated herein by reference.

FIELD OF THE INVENTION

This invention relates to percutaneous transcatheter and transapical cardiac valve implantation. More specifically, this invention relates to a device to better dilate the aortic valve leaflets than prior art and assess aortic valve annulus.

BACKGROUND OF THE INVENTION

Calcific aortic stenosis is a common cause of acquired valvular heart disease with substantial morbidity and mortality. Its incidence increases exponentially in older patient populations. Fibrosis, degeneration and subsequent calcification are no longer believed to be passive or purely degenerative in nature, but in fact are predominantly active processes mediated by underlying cellular mechanisms. Over time, as fibrosis and calcification worsens, valve leaflets become increasingly rigid, restricting their ability to open. This, in turn, impedes the antegrade flow of blood through the heart resulting in several clinical syndromes including progressive heart failure. Other causes of deformed and stenotic aortic valvular lesions include rheumatic heart disease, as well as nonacquired (i.e. congenital) heart disease. Initial stages of stenotic valvular heart conditions are well tolerated by the patient, but when leaflet restriction becomes severe, invasive measures such as aortic valve replacement have commonly been required.

With the advent of catheter-based cardiovascular procedures, minimally invasive balloon valvuloplasty techniques were developed to dilate stenosed valves, such as calcific, rheumatic and congenitally stenosed leaflets. During this procedure, a catheter having a deflated balloon is percutaneously inserted into a vein or artery and advanced until the balloon is positioned within the heart valve needing treatment. The balloon is then inflated to dilate the diseased valve opening, disrupting the rigid sheets of calcium and thereby permitting enhanced leaflet mobility. Balloon dilation, depending on the disease process, may result not only in the development of numerous flexible hinge points within fibrosed and calcified leaflets, but also separation of fused commissures. After the leaflets have been dilated, the balloon is deflated and removed from the patient's cardiovascular system.

Ideally, an infinite number of "hinge pointes" should be created circumferentially along the inner margin of the aortic valve annulus, from which the rigidly calcified leaflets arise. Retention of inflexible calcified ledges extending into the valve leaflets can prevent symmetric expansion and incomplete apposition of implanted stent valves against the annulus. This, in turn, may result in both peri and central valvular insufficiency of an inadequately deployed percutaneous stent-valve. Aggressive attempts to predilate with an oversized balloon can be complicated by an annular tear or rupture, resulting in potentially catastrophic and generally fatal complications. Predilatation with undersized balloons may avoid this complication but render the valve ill prepared for treatment.

In many current instances, valvuloplasty is performed with polymeric balloon catheters that can achieve relatively high pressures at a fixed diameter. Balloons made of non-distensible plastic materials are expanded using fluid pressure up to a certain diameter after which, increases in fluid pressure within the balloon produce very little change in balloon diameter. These balloons can achieve high pressures for an effective therapy, but have several inherent limitations.

For example, it is difficult to expand these balloons, and then return them to their pre-expansion configuration. The pre-expansion profile of these balloons can be somewhat reduced by prefolding during the manufacturing process. However, once inflated, the folded balloon segments are expanded within the vascular system. When deflated for removal, these segments arrange to a flattened state with a much larger profile, often called "winging". Withdrawal of these balloons therefore requires larger vascular introductory sheaths and thereby increases the risk of trauma to the vessels, resulting in compromised blood flow to an extremity or post operative bleeding. Additionally, non-distensible balloons also have thick cones—transitions from the cylindrical diameter to the catheter shaft diameter. These regions of the balloon make the catheter stiff, thereby increasing the risk of vascular trauma and increasing the difficulty of advancing through tortuous peripheral arterial anatomy.

Since the radial dimensions of the catheter balloon must greatly increase when inflated to achieve aortic valve dilation, a highly elastic material such as latex can be used to construct the balloon. Distensible balloons use these elastic materials and generally have excellent initial profiles and improved flexibility for introduction and travel through the vascular system. In addition, they possess good deflated profiles for removal from the vascular system. However, these highly elastic materials have significant limitations. For example, it may be difficult to control the expansion diameter of these balloons. The elastic materials continue to expand in diameter as pressure increases and therefore have no inherent limit on maximal diameter as with non-distensible balloons. Thus, distensible balloons can be unsafe for valvuloplasty, as the elastic limit can easily be exceeded when the balloon is fully inflated, potentially causing the balloon to rupture within the patient. Additionally, the balloon diameters can become too large for the valve being dilated causing rupture and tearing of both the valve and its adjacent structures.

In addition, prior art catheter balloons have been associated with mechanical injury to the cardiac chambers. For example, tissue near the ventricular apex may be injured due to the forceful longitudinal movement of the inflated balloon across the valve and within the cardiac chamber. In another example, sudden and unexpected movements of the balloon can cause further tissue damage. Blood and the vascular wall surface are inherently slippery against common catheter balloons which can result in significant balloon migration. As inflation fluid (e.g., contrast media) is introduced, the catheter balloon enlarges and eventually assumes a cylindrical or axial ovoid shape. This shape creates a tendency for the balloon to suddenly and uncontrollably pop in and out of the valve site and migrate deep into the left ventricle. In some situations, this sudden balloon movement following inflation can increase the difficulty to position the balloon accurately within the valve leaflets, cause tissue damage and even catastrophic puncturing of the left ventricle.

Further, typical catheter balloon shapes tend to completely obstruct the flow of blood through the heart while inflated. Without perfusion through or around the catheter, the catheter balloon inflation time is believe to be limited to a few seconds before risking complications due to profound hypotension.

A further disadvantage of prior art valvuloplasty balloons is its frequent failure to restore adequate flexibility to the aortic valve leaflets. That is, mere dilation with these previous balloon designs may not be enough to adequately open the severely fibrosed and calcified leaflets. The prior art balloon catheters are cylindrical in shape when fully inflated and thus have their maximal inflated diameter limited by the narrower sinotubular ridge and valve annulus at the distal and proximal margins respectively of the aortic root sinuses. Efforts to expand beyond these limits can result in tearing of the aortic valve annulus, catastrophic aortic insufficiency or rupture of the aortic root. In addition, traditional balloon catheter methods generally result in eventual restenosis of the aortic valve leaflets in 6-18 months, negating some or all of the regained flexibility.

Examples of some of these prior art catheter designs, as well as other related catheter designs are discussed and disclosed in the following U.S. Pat. Nos. 4,327,736; 4,777,951; 4,787,388; 4,878,495; 4,819,751; 4,909,252; 4,986,830; 5,352,199; and 5,947,924 and U.S. Pat. Publication No. 2005/0090846; the contents of all of which are incorporated by reference.

What is needed is a balloon valvuloplasty catheter that overcomes all of these disadvantages of the prior art. Indeed, what is needed is an invention that not only overcomes the disadvantages of the prior art in treating calcific aortic stenosis but also aortic stenosis resulting from congenitally abnormal valves and/or rheumatically injured valves.

SUMMARY OF THE INVENTION

One embodiment according to the present invention is directed to a dog-bone-shaped balloon catheter for performing valvuloplasty on a stenotic aortic or pulmonary valve or for opening up any stenotic constriction within a tubular member of the body. The tubular member could be, for example, any blood vessel of the body including a coronary artery, peripheral artery, veins of the body, esophagus, trachea, intestinal vessels, bile ducts, ureter, and the like. This embodiment has additional utility for use in predilatation of the aortic valve leaflets prior to placing a percutaneous aortic valve or other prosthetic device used for aortic valve repair, replacement, or implant. This embodiment may also be formed with a larger or smaller diameter balloon and used in arteries, veins, body orifices, or other hollow organs of the human body where dilatation along with a diameter measurement are needed. It provides advantages over the standard cylindrically-shaped valvuloplasty balloon due to the dog-bone shape for the balloon as well as the construction of the balloon.

Generally, the dog-bone shape allows the bulbous portions of the balloon to self-center on each side of the aortic annulus and position the narrower diameter waist adjacent to the annulus. The larger bulbous proximal end region of the balloon is positioned into contact with the aortic valve leaflets such that inflation of the balloon pushes the leaflets outward against the aortic sinus. The bulbous proximal portion of the balloon allows the aortic valve leaflets to be cracked or broken at or near their base and hyperextended outwards toward the sinus in a manner that provides greater benefit than that provided by a standard cylindrical balloon without the concern for dissecting the annulus. The narrow waist of the dog-bone balloon is formed such that the smaller diameter waist will not dissect the narrower annulus region. The distal bulbous region, which is located in the left ventricular outflow tract (LVOT), helps to prevent the balloon from migrating downstream during inflation due to blood pressure generated from the beating heart.

The dog-bone-shaped balloon of the present invention is preferably formed with a semi-compliant material in the smaller diameter waist region and with a non-compliant material for the proximal and distal bulbous end regions. The waist region functions to more accurately measure the diameter of the annulus than what can be attained using standard echocardiographic measurements. The waist also serves to measure the compliance characteristics of the annulus and thereby helps the physician to perform the valve dilatation procedure with a greater degree of safety to the patient against possible annular dissection. Inaccuracies with the standard echo measurements exist due in part to the anatomically oval shape of the annulus which results in typically undersized estimates for the diameter of the annulus. Such undersizing often can lead to incorrect sizing of the percutaneous valve and resultant poor valve function. The semi-compliant waist of the present invention is able to firmly contact the oval waist, readjust its shape, and provide a more accurate measurement of its true diameter while ensuring that the annulus is not exposed to dilating forces that could cause annular dissection.

The semi-compliant waist preferably has an equilibrium diameter at approx 0.1-0.2 atm of internal pressure that is smaller in diameter than the annulus diameter; the bulbous proximal and distal end regions are sized to make full contact with the valve leaflets and the LVOT, respectively. Thus as the balloon is initially inflated across the annulus, it tends to self-center with the bulbous regions on each side of the annulus. As fluid is further injected into the balloon, the internal balloon pressure increases as the diameter of the waist increases in accordance with the compliance curve defined by the semi-compliant waist material and method of construction. When the internal balloon pressure reaches approx 2 atm, the leaflets of a vast majority of patients will have been pushed outwards against the aortic sinus by the proximal bulbous region. At a pressure of approx 2 atm the distal bulbous balloon region lodges in the LVOT upstream of the annulus and any anatomical obstructions found in the LVOT are pushed outward by this bulbous portion. The waist enlarges in diameter and defines the low end of the annulus diameter for which this balloon is intended to be used.

Further injection of fluid volume into the balloon can occur until the balloon waist enlarges further and comes into contact with the annulus. The relative volume that has been injected into the balloon has been continuously monitored by measuring the movement of a syringe plunger of an inflation device. The internal pressure within the balloon is monitored via a pressure transducer located within the balloon and measures an inflection in the rate of pressure increase per change in volume injected into the balloon. At this inflection point the slope of change in pressure versus change in volume curve changes to a steeper slope that is reflective of the compliance of the annulus plus the balloon waist. The pressure at this inflection point corresponds to the diameter of the waist and therefore measures the diameter of the annulus. Although the waist may come into full contact with the annulus, it does not provide an outward force that could contribute to annular dissection since the resilient, elastic, semi-compliant waist resists the approx. 2 atm of internal balloon pressure.

It is noted that the inflection point or change in slope of the pressure versus volume curve may be enhanced by making the bulbous portions of the balloon non-compliant. Thus as fluid is injected following contact of the waist with the annulus, these bulbous end regions cannot increase in volume and hence it is the compliance of the annulus and waist that is being observed.

Further injection of fluid into the balloon can further provide additional outward force in the proximal bulbous region to push the leaflets outward at an even higher force up to 3 or 4 atm or possibly higher. The curve of the change in pressure versus change in volume injected continues to follow a slope indicative of the annulus plus the waist. The forces pushing outwards against the annulus however remain lower than the internal balloon pressure. For example, if contact of the waist with the annulus was made at 2 atm, then an internal pressure of 3 atm will apply a force of only 1 atm against the annulus, thus providing this embodiment with a safety against causing annular dissection. The present invention has the ability to apply pressure onto the annulus in a more controlled manner due to the restraining force provided by the semicompliant waist. This applied pressure that is placed onto the annulus is available to the physician following waist contact with the annulus as identified by the presence of the inflection point. The slope of the pressure versus volume curve following contact of the waist with the annulus also allows the physician to assess the strength and stiffness of the annulus.

Other methods are possible for measuring the waist diameter and hence the annulus diameter at the inflection point. In one method the balloon is inflated with contrast fluid that is visible under x-ray fluoroscopy; also radiopaque markers placed on the balloon can be visualized by fluoroscopy. As the balloon comes into contact with the annulus as identified by an inflection point as described earlier, fluoroscopy is used to measure the diameter of the waist and hence indicate the diameter of the annulus. In another method a piezoelectric material know in the industry for measuring tension is placed around at least a portion of the waist circumference. Stretching this piezoelectric material to a greater extent will result in a proportional electrical signal that is indicative of the diameter of the waist. At the inflection point, the electrical signal would reflect the diameter of the waist and hence the annulus diameter.

An alternate method for measuring waist diameter can be accomplished by placing an electrically resistive material around at least a portion of the circumference of the waist. Expansion of the waist will result in a change in resistance that is indicative of the waist diameter. Other means such as capacitive or inductively coupled sensors can be placed along a portion of a circumferential path around the balloon waist. These sensors are capable of detecting distances or separation from one sensor to another and can be used to identify the waist diameter at the inflection point. An ultrasound sensor can also be place within the interior of the balloon and used to sense the edges of the balloon or edges or perimeter of the annulus when the waist comes into contact with the annulus. Such intravascular ultrasound technology is currently being used in the industry for measuring diameters of coronary and peripheral blood vessel and can be located on the guidewire shaft that extends through the center of the balloon.

In one embodiment, the inflation tool used to inject fluid into the dog-bone-shaped balloon catheter of the present invention is a disposable, hand operated, syringe-like device. The tool is fluidly connected to the balloon catheter and electrically connected via wire or RF signal to a pressure transducer or other sensor such as those previously described located in or on the balloon or within the catheter shaft near the balloon. A variable resistor or other means is used to detect a change in movement of the syringe plunger with respect to the syringe barrel. Since the inflation tool is hand operated, variability can occur in the rate of delivery of fluid to the balloon catheter. An additional pressure transducer may be located within the syringe barrel to account for inertial and compliance effects that could alter the accuracy of the balloon pressure and volume delivery measurement during the inflation of the balloon. A display located on the inflation tool indicates the balloon pressure, the pressure when the waist contacts the annulus, and the diameter of the waist and hence the annulus diameter at the inflection point.

The inflation tool is able to deliver the initial approximately 90-98% of the fluid volume to fill the balloon to an equilibrium volume and shape at a low internal balloon pressure of approx 0.1-0.2 atm in approx 1-5 seconds. The second portion of the balloon filling is performed over the next 1-5 seconds to allow for a more controlled and steady delivery of fluid to the balloon and a greater ability of observing the inflection point as indicative of a change in slope of the pressure versus volume delivery curve. The inflation tool has two plungers that allow the balloon to fill rapidly to an equilibrium size to shorten the time that the balloon is being inflated and depriving the patient from blood flow through his LVOT. The plungers also restrict the flow from being delivered too rapidly when the inflection point is being observed. One plunger has a one-way valve to allow the fluid to be rapidly removed from the balloon following the inflation period.

Several methods are described for forming a balloon having a semi-compliant waist and non-compliant bulbous end regions. In one embodiment a semi-compliant dog-bone balloon is formed with a resilient or elastic material such as polyurethane or other thermoplastic elastomeric polymer. The waist can be supported using a braid, axial fibers, or slotted material to prevent the waist from extending axially during the expansion of the balloon. The bulbous end regions are further supported by applying a non-compliant material such as polyethylene terephthalate (PET) to the outside or within the bulbous end regions to reduce volume expansion of these regions. In another embodiment coextrusions of semi-compliant and non-compliant materials are also described as part of a potential method for forming the dog-bone-shaped balloons. Several other methods for forming the balloon are contemplated.

Additional embodiments of dog-bone and non-dog-bone shaped balloons are also possible. These embodiments offer some advantages over the standard cylindrical balloon currently used for valvuloplasty but may have some disadvantages over the preferred embodiment having a semi-compliant waist and non-compliant bulbous regions.

Additional embodiments include a balloon formed entirely from a non-compliant material or entirely a semi-compliant material and having a dog-bone shape are possible and are expected to have improved positioning characteristics across the annulus and ability to hyperextend the aortic valve leaflets compared to standard cylindrical balloons. The non-compliant balloon generally will not have the ability to measure the diameter of the annulus via pressure sensing without applying the entire internal balloon pressure to the annulus. The semi-compliant balloon generally will not have a sharp inflection point due to the ability of the bulbous end regions to grow in volume as fluid is injected thereby not causing an abrupt change in the slope of the pressure versus volume curve. Also as one continued to increase the internal balloon pressure to attain contact of the waist with the annulus to measure the annulus diameter, the bulbous proximal end region could be growing in size in an uncontrolled manner resulting in potential dissection in the sinus region.

A further embodiment is directed to a dog-bone-shaped balloon with a non-compliant waist and semi-compliant end regions. This balloon provides for improved positioning across the annulus over a standard cylindrical balloon but is unable to provide a measurement via pressure measurement for the annular diameter in a manner described for the semi-compliant waist. The bulbous regions may be exposed to varying pressure increments to hyperextend the aortic valve leaflets to an extent that is appropriate to a specific patient as identified under fluoroscopy.

Yet a further embodiment is a valvuloplasty balloon catheter that is comprised of two separate balloons one contained inside of the other balloon. The inner balloon is a smaller balloon that has a relatively abrupt profile such that it can locate well in the pocket that is typically found just upstream of the aortic valve annulus. This smaller inner balloon is inflated initially to position the balloon catheter properly across the annulus. Immediately after the catheter is positioned, the second larger outer balloon is inflated to cause the proximal aspect of the outer balloon to push the leaflets outwards against the wall of the sinus. The distal portion of the outer balloon can be of variable length and can be cylindrical in shape. The proximal and distal aspects of the outer balloon can also form a dog-bone shape and can take on the characteristics of any of the dog-bone embodiments described in this disclosure including being formed from semi-compliant and non-compliant materials.

An additional embodiment for a valvuloplasty balloon has the feature of providing perfusion to the patient while the balloon is inflated. During inflation within the LVOT, standard balloons block blood flow to the head and other organs of the body. To mitigate this concern, the standard balloons are inflated for only approx 10-15 seconds while the patient is undergoing rapid pacing to temporarily reduce his left ventricular pumping output. A perfusion balloon allows the dilation of the aortic valve leaflets to occur over a period of minutes instead of seconds and would obviate the need for rapid pacing. A perfusion balloon may be used to more effectively deliver drugs that could help maintain native valvular function and reduce valvular restenosis. Other methods such as using cryotechnology or ultrasound may be more effectively administered to the patient in order to treat the plaque or calcium buildup that occurs in patients with aortic valve stenosis in conjunction with the perfusion balloon.

The perfusion balloon of the present invention has multiple small balloons, approximately five, that are arranged such that they touch each other and form a circle. The balloon can be bonded to each other along the lines with which they make contact. Inflation fluid is manifolded into each of the five balloons on the proximal end and the distal ends of each of the balloons is blocked off. The central region between the five balloons is used to provide a passage for blood flow. The support for this structure is derived from the contact of one balloon to the next. The internal blood flow perfusion area for a typically sized aortic valve would be approximately 0.4 cm squared.

In another embodiment of the perfusion balloon, an external wrap is placed around the five previously described balloons. This outer wrap serves to further bond or hold the five balloons into apposition with each other but also to provide a compartment between the outer wrap and the five balloons. This outer compartment can be exposed to internal pressure from a fluid and can be used to provide dilatation capabilities to the valve leaflets. The outer compartment can be formed into a dog-bone shape if desired and the characteristics of the other embodiments described in this disclosure can be applied to this outer dog-bone-shaped balloon outer wrap or covering. An internal wrap can also be located in the central region between the five balloons. This internal wrap can serve as a flow conduit path for blood perfusion and can also be attached to each of the five balloons to provide stability to the overall perfusion balloon structure.

Methods for forming the perfusion balloon are also described. One can form the equivalent of five individual balloons by using a forming tool and two balloons having a larger and smaller diameter. The larger diameter balloon forms approximately the outer half of each of the five balloons and the smaller balloon forms the inner half of each of the five balloons. The manifold of the inflation fluid from one balloon portion to another portion can be accomplished using techniques that will not compromise balloon integrity. A temporary valve can be located in the central perfusion area to ensure that systemic blood pressure is maintained during the inflation procedure.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

DETAILED DESCRIPTION OF EMBODIMENTS

Figure 1:
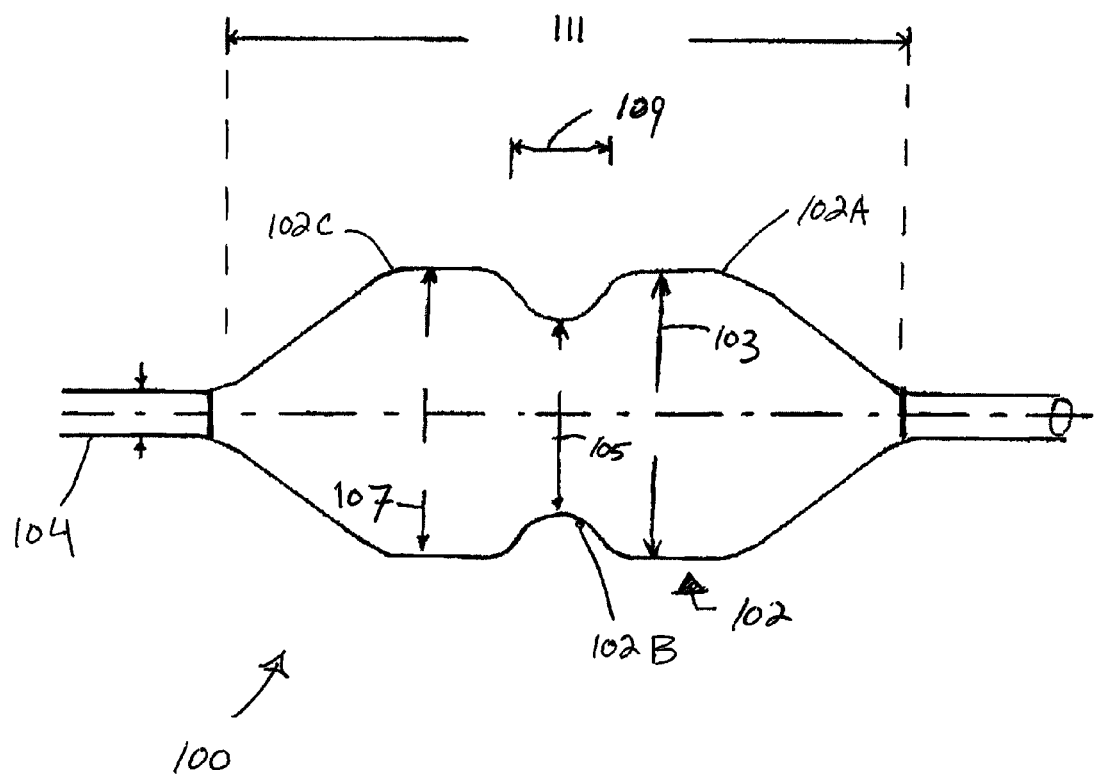
FIG. 1 illustrates a side view of a balloon catheter according to the present invention.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

FIGS. 1-4 illustrate a preferred embodiment of an aortic valvuloplasty catheter 100 with a non-compliant proximal region 102C, a non-compliant distal region 102A a semi-compliant waist 102B according to the present invention. The semi-compliant waist is formed of a resilient elastomeric material that can return to its initial shape after multiple inflations. Generally, these regions 102A, 102B and 102C inflate to a dog bone or hourglass shape at certain inflation pressures to help achieve a desired position of the balloon 102 within the aortic valve 120. As described in greater detail below, the semi-compliant waist 102B can further expand against the annulus 118 of the valve 120, helping the user determine the size of the annulus 118 and thus an appropriate replacement valve size.

The valvuloplasty balloon 102 is preferably disposed on a distal end of a catheter body 104, and delivered over a pigtail-end guidewire 106. At least one passage within the catheter body 104 is in communication with the balloon 102 to allow inflation by liquid (or optionally gas).

It should be understood that the present valvuloplasty catheter 100 can be created and used according to the techniques set forth in U.S. Patent Publication No. 2005/0090846, the contents of which are incorporated by reference.

In operation, the valvuloplasty catheter 100 of the present invention is introduced through the femoral or brachial artery using a Seldinger technique to place a vascular sheath introducer in the peripheral vessel. Alternately, the valvuloplasty balloon catheter of the present invention can be placed transapically antegrade across the aortic valve via a surgical intercostal incision. For the transapical approach the distal bulb of the dog-bone-shaped balloon would be placed into the aortic sinus rather than the proximal bulb as when using the transfemoral approach. For the sake of simplicity, all further description will be made with respect to the transfemoral approach. However, it should be understood that a variety of different placement procedures are possible according to the present invention.

Returning to the transfemoral approach, a guidewire is placed across the aortic valve and the valvuloplasty balloon catheter 100 is advanced retrograde over the guidewire such that the pigtail 106 is positioned in the left ventricle. Next, using fluoroscopy or other imaging techniques, the balloon 102 is placed within the valve 120 so that the distal portion 102A is positioned in the left ventricle outflow tract 114, the waist 102B is positioned at the annulus 118 and the proximal portion is positioned against the leaflets 116 in the aortic sinus 112.

Figure 2:
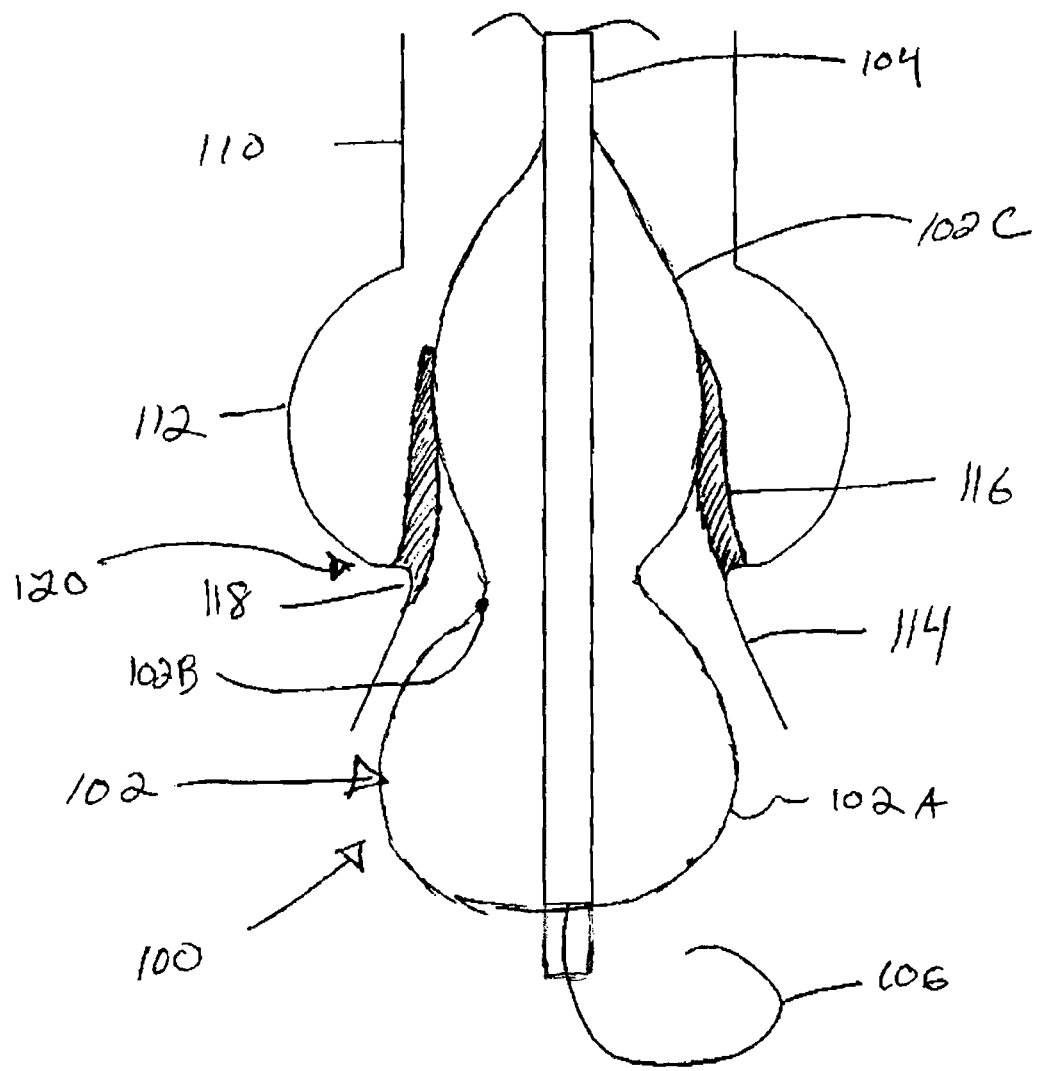
FIG. 2 illustrates the balloon catheter of FIG. 1 in a first state of inflation according to the present invention.

As seen best in FIG. 2, the balloon 102 is inflated to a pressure of approximately 0.1 to 0.5 ATM (i.e., the pressure inside the balloon 102 is slightly higher than the pressure outside of it, about 0.2 ATM). At this pressure, the waist 102B is prominently undersized relative to the proximal portion 102C and the distal portion 102A as well as the annulus 118. This undersized waist 102B helps "center" or position the waist 102B at the annulus 118 and therefore achieve desired positions of all portions of the balloon 102. A slippery agent such as silicone oil or a hydrophilic coating can be applied to the exterior surface of the balloon to enhance this centered orientation. Alternately the outside surface of a portion of the balloon can be textured or roughened to help hold the balloon in position following inflation.

Figure 3:
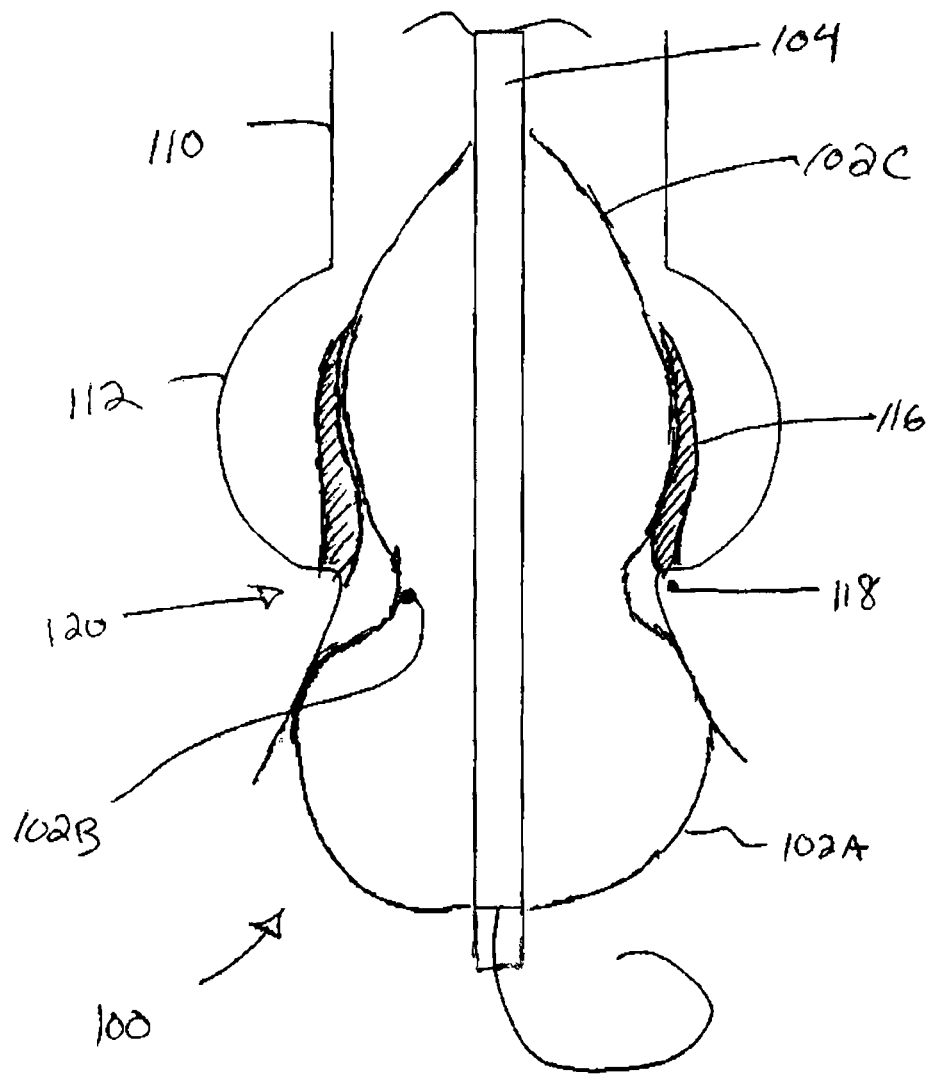
FIG. 3 illustrates the balloon catheter of FIG. 1 in a second state of inflation.

Next, the pressure in the balloon 102 is further increased; causing the size of the proximal portion 102C to increase as shown in FIG. 3 and begin to push the leaflets outwards. This pressure can range between 0.5 and 5 ATM and preferably between 1-2 ATM. The size increase of the proximal portion 102C pushes the valve leaflets 116 open, cracking the calcified portions and further creating hinge points.

The waist region 102B also increases in diameter at the previously mentioned pressure due to the compliant nature of the material in this area. The distal portion 102A may further increase somewhat in size, depending on variation in the anatomical features in the outflow tract. However, the expansion of the distal portion 102A is ultimately limited by the non-compliant material construction. Since the blood flow can only be blocked for a short period of time, the balloon 102 is quickly deflated after a short period of time.

After the leaflets 116 have been "hinged" to an acceptable amount, the user can use the catheter 100 to estimate the size of the annulus 118 when subjected to an internal dilating load and therefore determine the appropriate size of the replacement valve to implant. The following methods are described to help determine the fully stretched diameter of the annulus 118.

Figure 4:
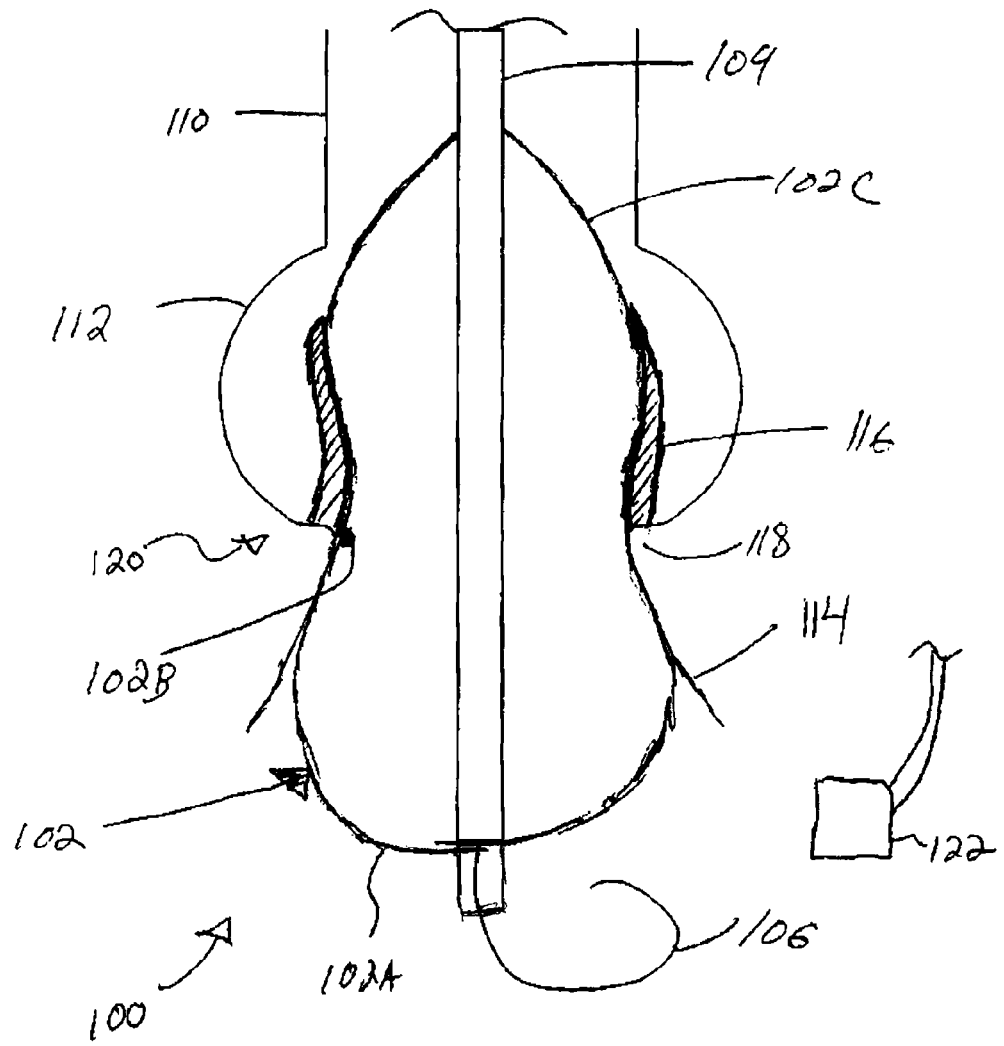
FIG. 4 illustrates the balloon catheter of FIG. 1 in a third state of inflation.

Preferably, to determine the valve stretch diameter, the pressure within the balloon 102 is once again increased to expand the balloon 102 beyond that shown in FIG. 3 to that of FIG. 4. Contrast liquid is injected into the balloon 102 to allow it to show up on imaging devices (e.g., fluoroscopy, x-rays, etc.). Since the waist 102B is composed of a semi-compliant material, the further increased pressure causes the waist 102B to extend outward. The proximal region 102C and distal region 102A remain at relatively the same diameter because these regions are constructed with a non-compliant material. As the pressure increases, the waist 102B extends radially outward until it contacts the annulus 118 as seen in FIG. 4.

Once the waist 102B has reached the annulus 118, the valve 120 can be imaged. This image illustrates the contrast liquid in the balloon 102 and therefore the shape of the waist 102B, which can be visualized and measured. Alternately, radiopaque markers may be embedded or otherwise located at the waist 102B for fluoroscopic imaging purposes.

The user can help determine when the waist 102B has reached the annulus 118 by monitoring the change in pressure within the balloon 102 versus the change in balloon volume, or the change in pressure versus time if the volume rate of infusion of fluid into the balloon is maintained at a constant rate. A pressure manometer 122 or a pressure transducer can be connected in parallel with an inflation syringe at the proximal end of the catheter 100. Alternately a pressure transducer located in or near the balloon or in fluid communication with the balloon can also provide a pressure measurement. The pressure transducer can be a wireless transducer if desired. In this case an RF signal can be sent from the transducer to a receiver located outside the body of the patient to indicate pressure within the balloon.

Figure 5:
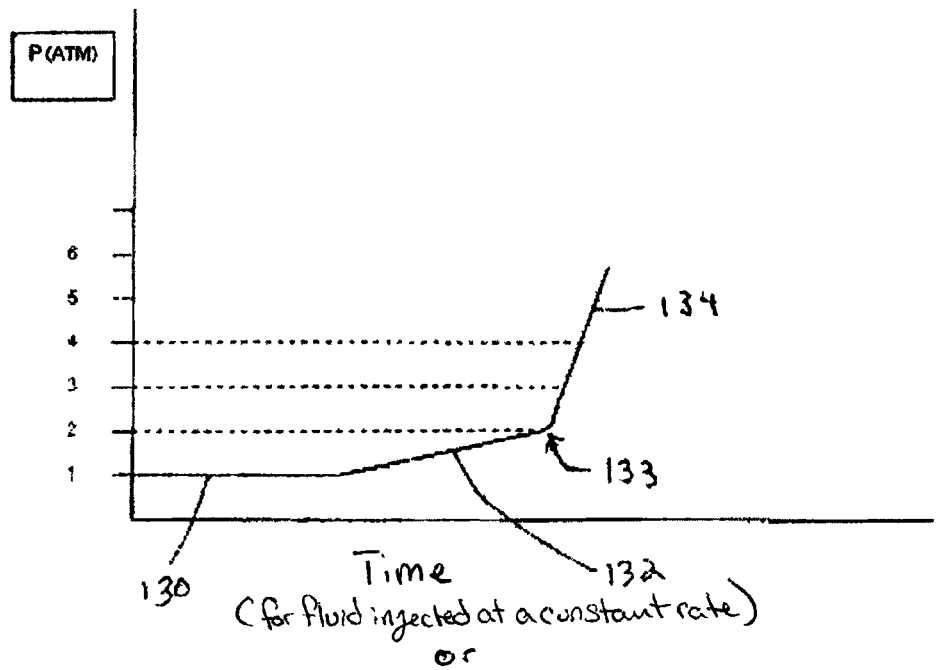
FIG. 5 illustrates an example pressure inflation curve of the balloon catheter of FIG. 1.

FIG. 5 illustrates an example graph that illustrates how pressure may change in an example balloon 102 over time as fluid volume is injected into the balloon at a constant rate or versus balloon volume. As the balloon 102 initially inflates, the proximal region 102C and distal region 102A inflate and the waist inflates to its equilibrium, low pressure, state. Since these regions 102A and 102C are composed of non-compliant materials, the pressure within the balloon 102 remains relatively unchanged as the unconstrained balloon begins to fill with fluid (e.g., pressure slope 130 is relatively flat and at a low pressure). As the proximal region 102C and distal region 102A reach the limit of their non-compliant expansion, the pressure within the balloon begins to increase (e.g., relatively increasing pressure slope 132) causing the waist 102B to expand beyond its equilibrium, low pressure, state. This pressure change during the expansion of the waist 102B generally follows a low upward slope 132 indicative of the compliance of the waist material until the waist 102B contacts the annulus 118, which significantly limits further expansion of the waist 102B. Therefore, the annulus 118 causes in an inflection point 133 in the pressure versus relative or absolute balloon volume curve followed by an increase in the slope 134 that is indicative of the compliance of the annulus and the waist. The absolute volume of the balloon can be controlled by a constant volume pump and monitored to track the absolute volume injected into the balloon. Alternately, the constant volume pump can be used to control the relative volume of fluid injected into the balloon and the relative volume change can be plotted versus relative change in balloon pressure. If the fluid is injected into the balloon at a constant rate, then the slope 134 for the slope of FIG. 4 can represent the change in pressure versus time after contact is made for the waist with the annulus.

The physician or operator has the capability with the present invention of providing a controlled valvuloplasty procedure with application of a controlled force being applied to the annulus. As the balloon waist comes into contact with annulus, the inflection point or change in slope of the pressure curve as shown in FIG. 5 is observed. At this point the pressure force within the waist is balanced by the constrictive force of the waist and very little force is being applied to the annulus. The physician or operator can continue to increase the pressure within the balloon and thereby apply only this incremental pressure above the inflection point pressure to the annulus. Since only this incremental pressure is being applied to the annulus, the annulus is protected against dissection that can occur if it were exposed to a large force. The slope of the pressure curve above the inflection point is also indicative of whether the annulus is a softer annulus or whether it is hard and calcified. Therefore the physician or operator is able to assess the effective modulus of the annulus by observing the slope of the pressure curve above the inflection point.

In this respect, when the user determines that the slope of the pressure changes from a slope similar to slope 132 to slope 134 (i.e., the inflection point 133), the waist 102B has likely contacted the annulus 118. At that point, the user can image the valve 120 as previously described to determine the annulus diameter. Alternately, the user or manufacture may determine the size of the waist 102B of balloon 102 at different pressures prior to a procedure. Therefore, the user can look at the pressure reading for the inflection point 133 to estimate the size of the waist 102B.

Preferably, a computer and computer software (e.g., specialized pressure display device or a PC) can be used to record and display the pressure in the form of a graph. The user can monitor the graph to manually determine the inflection point 133 and therefore the size of the annulus. Alternately, the computer software may monitor pressure data (e.g., the slope) and automatically determine the inflection point 133 and convert that pressure value to a diameter size.

Figure 6:
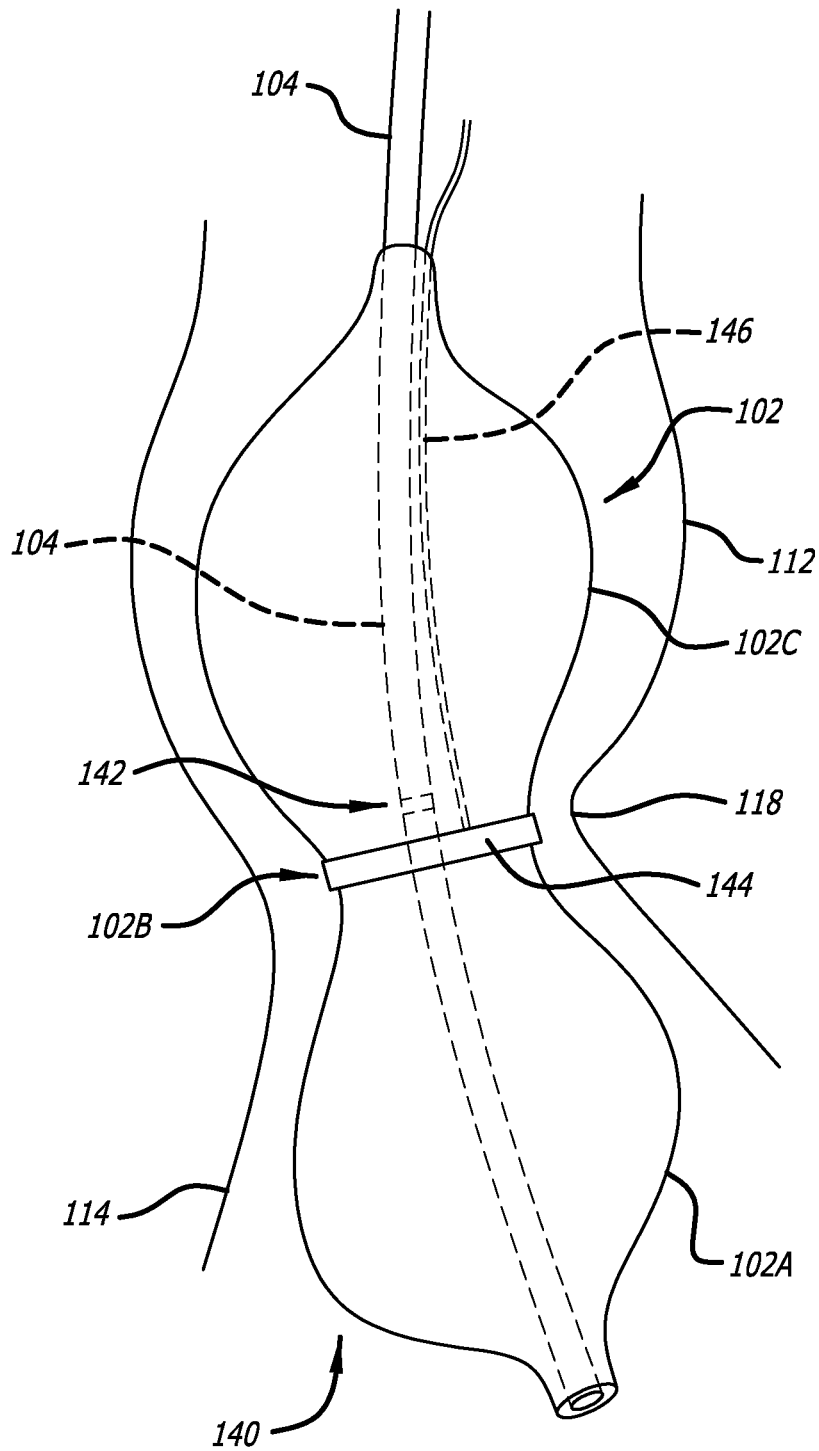
FIG. 6 illustrates an side view of a balloon catheter and diameter sensing device according to the present invention.

FIG. 6 illustrates another preferred embodiment of an aortic valvuloplasty catheter 142 that is also capable of measuring the diameter of the annulus 118 of the valve. Generally, the valvuloplasty catheter 142 is similar to catheter 100 shown in FIGS. 1-4. A sensor 144 can be located at or around the waist 102B of the balloon 102 to measure the expansion.

For example, the sensor 144 may include a resistive material formed into a ring around the waist region 102B or a portion of the waist region as shown in FIG. 6. Upon stretching of the waist 102B, the resistance of the material changes and can be detected using a circuit that monitors change in electrical resistance. In another example, the sensor 144 may be a piezoelectric material located around a portion of the waist such that an electrical signal can be generated as the material is forced to stretch to varying degrees.

Either of these previously mentioned sensors 144 are preferably connected to an electrical wire 146 located along the shaft 104 of the balloon to deliver the signal from the balloon 102 to the proximal end of the balloon catheter 140 and to an inflation device that is attached to the balloon catheter.

In another example, the sensor 144 may include either capacitive coupled or inductively coupled sensors that detect the proximity of one sensor to another and are able to identify changes in the separation between two such sensors. More specifically, components of the sensor may be located both at the balloon waist 102B and within the diameter of the waist 102B, on the shaft 104. Hence, as the waist 102B expands, the components of the sensors move apart from each other and can therefore be measured.

In yet another example, ultrasound sensor 142 can be used to measure the diameter of the waist 102B as it contacts the annulus (e.g., as evidenced by the inflection point 133 in the slope of the pressure versus volume curve). Small ultrasound sensors 142 are located in the interior of the balloon along the catheter shaft 104. Such ultrasound sensors are used in interventional balloon catheters and in other diagnostic devices to measure vessel diameter or the diameter of surrounding structures. The diameter measured by these sensors 142 during the inflection point 133 is then indicative of the diameter of the annulus 118. The ultrasound sensor 142 may also be capable of identifying the perimeter of the annulus and this information can be converted to an annulus diameter.

In a preferred embodiment, the distal portion 102A achieves maximum predetermined diameter at approximately 0.3-1 ATM. The proximal portion 102C achieves its maximum predetermined diameter after the pressure has caused the leaflets to become displaced outwards at approximately 0.5-2 ATM. Preferably, the catheter 100 (or catheter 140) is configured to not exceed approximately 3-5 ATM of pressure so as to remain safely contained by known dilatation balloon materials.

Figure 7:
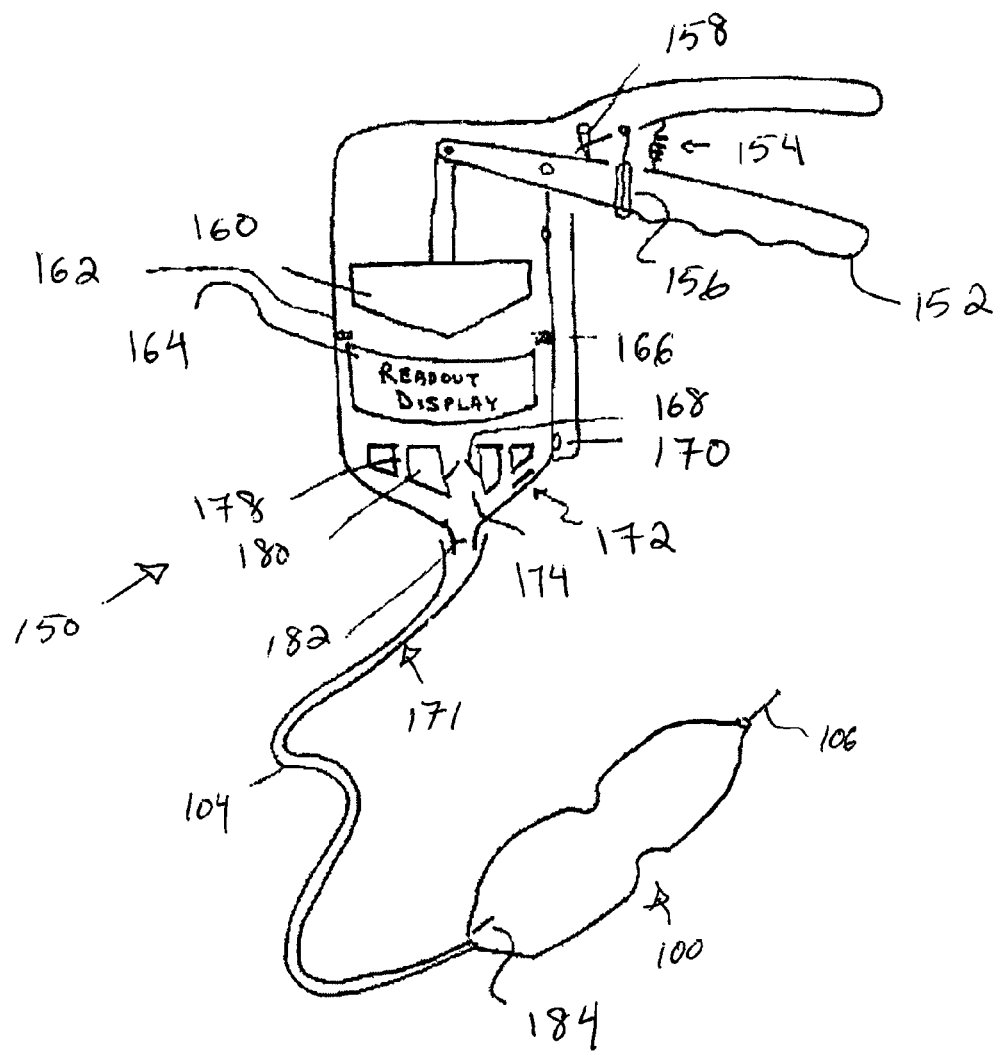
FIG. 7 illustrates an inflation device according to the present invention.

A desired pressure limit (e.g., 3-5 ATM) within the balloon 102 can be achieved with the inflation device 150 shown in FIG. 7 (described elsewhere in this specification). For example, a cutoff safety or pressure spill-off valve contained in a balloon inflation device can be activated at a desired maximum pressure.

In one balloon embodiment, the waist 102B assumes an oval shape when inflated to better engage the generally non-circular valve cross section of the annulus 118. The waist 102B can cause the annulus to become round as it comes into contact with it or applies an outward force against the annulus as the annulus becomes rounded. The force applied by the waist outward onto the annulus is, however, less than the internal pressure of the balloon since the semi-compliant waist 102B is providing an inward constrictive force that acts to balance the outward acting internal pressure. The entire internal balloon pressure also acts to cause the leaflets to be pushed outward into the sinus region.

Preferably, the proximal region 102C has an inflation diameter that is sized similarly but slightly smaller than the aortic sinus 112 that is located adjacent to the ascending aorta 110. This diameter size of the proximal bulbous region 102C provides greater distension to the leaflets 116 and thereby more effectively crack the calcium deposits than could be attained with a standard cylindrically shaped balloon.

Alternately, the balloon 102 can be constructed such that when a specified volume of fluid is place within its interior, the waist diameter is directly known. Thus by controlling and knowing the volume of inflation fluid that is delivered into the balloon along with monitoring the pressure within the balloon, the waist diameter can be determined (by knowing the volume) when the waist comes into contact with the annulus (by monitoring the pressure and noting the inflection point). A positive displacement fluid delivery device such as a syringe can be used to assess the volume of fluid delivered to the balloon. A pressure graph similar to FIG. 5 can be created for monitoring purposes in which the y-axis again represents the balloon pressure but the x-axis represents the absolute volume delivered to the balloon rather than a relative volume delivered when the inflation fluid is delivered at a constant rate.

FIG. 7 illustrates an inflation tool 150 according to the present invention used to deliver contrast fluid to the valvuloplasty balloon 100. Compression of a handle 152 drives a plunger 160 down a barrel 152 to force the contrast fluid into the valvuloplasty catheter 171. As the lowered plunger 160 near the stops 166, contrast fluid is driven in a two stage process.

In the first stage, contrast fluid travels at a rapid rate out of the outflow port 182 to fill the balloon 100 with approximately 90% of its balloon volume in approximately 1-5 seconds. In the second stage, the top plunger then drives the remaining about 1-2 cc of fluid through the side holes 178 located in the lower plunger at a controlled rate that is limited by fluid resistance through the holes 178.

To remove the fluid from the balloon 100, a toggle switch 158 is activated to allow a compression of the handle 152 to force the plunger upward instead of downward, creating a vacuum that causes the contrast fluid to be removed rapidly through the one way valve 168 located in the lower plunger 180. The lower plunger 180 rides upward from the vacuum force until it comes into contact with the stops 166 and is ready for the next deliver of fluid to the balloon.

A variable resistor 156 serves as a fluid volume measure to track the relative amount of fluid delivery (or change in volume delivered) to the balloon 100. Other digital position sensors can also be used to detect the relative movement of the plunger with respect to the barrel of the delivery device. The sensor that detects fluid volume change in the barrel sends an electrical signal to the display 164 located on the inflation device, the balloon catheter, or on a separate member located outside of the patients body.

A balloon pressure transducer 184 is located in the balloon 100 near the junction with the catheter shaft 104. A barrel pressure transducer 172 is also located in the delivery device or in the barrel 162 of the inflation tool in order to account for balloon pressure variability due to inertia and shaft compliance. Only one of the pressure transducers may be needed to ensure that the pressure reading is an accurate measure of the balloon pressure. The pressure reading representative of the balloon pressure and the relative balloon volume are detected by a readout display 164. The readout display comprises a computer chip along with the electronic circuitry to receive the pressure and relative balloon volume signals, store them, and plot pressure versus relative or absolute balloon volume. The computer chip also computes the slope of the pressure versus volume curve and is able to detect a change in this slope.

When the slope of the pressure versus volume curve reaches an inflection point or a change in slope, this detected pressure will be captured by the computer chip and displayed along with the diameter of the balloon at this pressure. The diameter of the balloon will be calculated by the computer chip and is reflective of the modulus of the waist region and the pressure at the inflection point. This waist diameter will then indicate the annulus diameter which will be displayed by the readout display.

It is further noted that the inflation device can also be operated such that fluid is delivered to the balloon catheter at approximately a constant rate. In this case the computer chip found in the readout display would be receiving pressure data and storing it versus time elapsed since the start of fluid injection into the balloon. The computer chip would in this instance plot pressure versus time and would compute the slope of this curve and detect a change in this slope. When the slope of the pressure versus time curve reaches an inflection point, the pressure at this point is captured by the computer chip and is converted to a waist diameter reading that is displayed by the readout display.

Preferably, the balloon 102 comprises a single internal compartment. However, multiple compartments with their own inflation lumens are also possible. For example, the balloon 102 may include a proximal compartment, a middle waist compartment and a distal compartment, each allowing for individual inflation control.

The balloon 102 can be made from a variety of different materials known in the art for use in balloon catheters. For example, compliant or semi-compliant material can be selected from nylon, Surlyn, vinyl, PVC, polyethylene, polyurethane, Pebax, olefins or copolymers of these materials. In another example, non-compliant material can be selected from PET (Dacron), Teflon, polyimide, Kevlar wraps, metal, polymer or fibrous material. In a further example, compliant or semi-compliant material can be made to be relatively non-compliant by applying crosslinking such as ebeam, chemical or other crosslinking treatments. In yet another example, a non-compliant material can be made more compliant or semi-compliant by treating it with ebeam, chemical treatment or other process to weaken the molecular structure of the balloon material.

In one embodiment, the outside of the balloon 102 can be coated with a desired drug for elution during a procedure. For example, olimus or paclitaxel type drugs could be used or other types of drugs to offset the local deposit of calcium and possibly alter osteoblast calcium deposition.

As previously described, the balloon embodiments of the present invention may have regions of different compliance (e.g., non-compliant, semi-compliant and compliant). Some example techniques for creating balloons with these characteristics are described in greater detail below.

Figure 8:
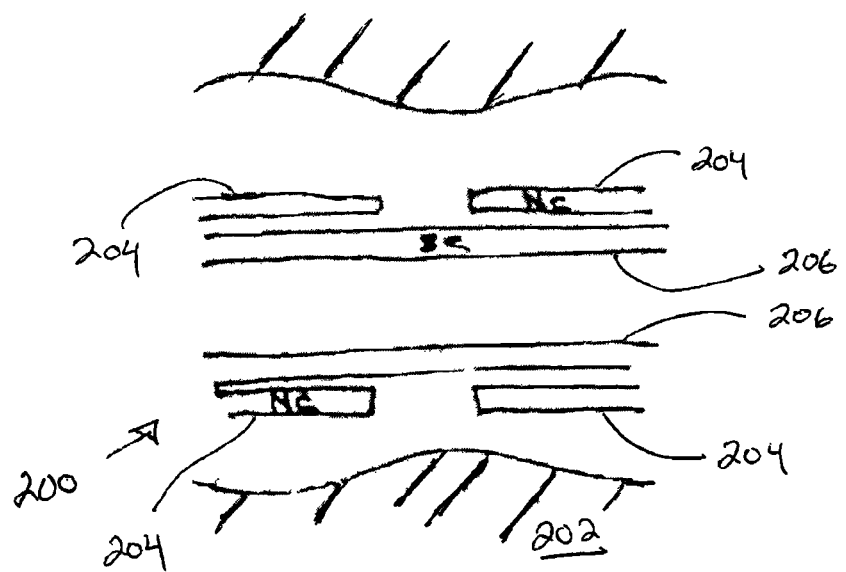
FIGS. 8-15 illustrate various techniques for providing balloon regions with different compliancy according to the present invention.

In one example shown in FIG. 8, a balloon 200 can be created by extruding a first tube 206 of semi-compliant material and a second tube of non-compliant material 204. One or more segments of the non-compliant tubing 204 can be placed over the semi-compliant tubing 206 concentrically in the region or regions that are to be non-compliant (e.g., proximal section 102C and distal section 102A). This tubing assembly is then placed into a heated mold 202 that forms the external shape of the balloon 200 while pressure, internal to the tube assembly, is also applied to maintain desired contact with the mold contours. An adhesive agent or thin polymer layer can also be applied between the concentric tubes 204 and 206 (preferably prior to the mold process) to enhance bonding to each other.

Additionally, axially oriented fibers can be adhered or embedded across the waist region to help reduce axial length increase in the waist as the balloon 200 is exposed to increasing pressures. The axial strands can be individual polymeric or metallic strands or multifilament strands that are bonded to the outside of the waist region. Alternately, the strands can be sandwiched between two layers of balloon material.

Figure 9:
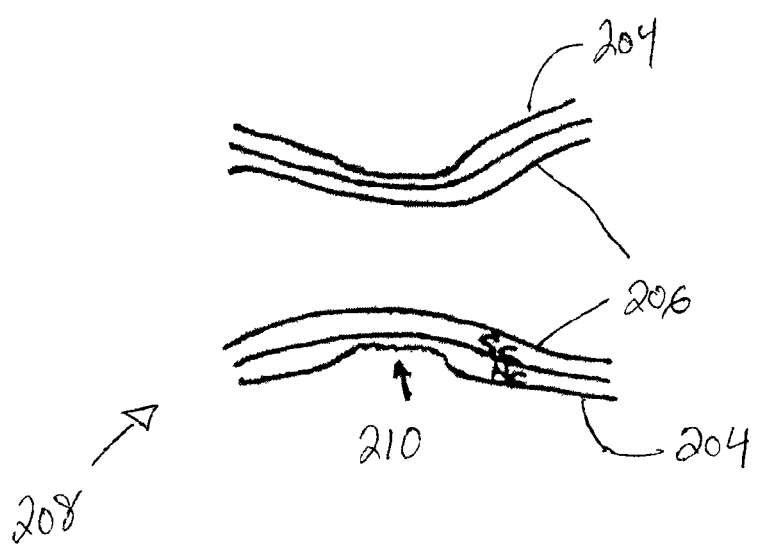

In another example seen in FIG. 9, a balloon 208 can be created by coextruding two tubes having an inner tube 206 with semi-compliant material and an outer tube 204 having non-compliant material. A portion of the outer, non-compliant tube 204 can be etched away in a region desired to be semi-compliant (e.g., the waist 102B). Preferably, laser etching, plasma etching, mechanical etching or chemical etching are used. The non-compliant tube 204 can be partially etched through or fully etched through, leaving the semi-compliant tube exposed 206. Next, the coextruded tubes are placed in a heated mold where pressure internal to the tube presses the tube against the mold contours to form the desired mold shape. Alternately, the coextruded tubes can be molded prior to etching of the non-compliant material 204. After molding, the outer tube can be further etched in locations to more precisely achieve a desired compliance (or non-compliance).

In another example construction method, a non-compliant outer layer can be applied over the outside of the entire semi-compliant balloon and axial slits located in the waist region can be formed in the outer non-compliant layer in the waist to allow the semi-compliant waist to enlarge in diameter when exposed to increasing internal pressure.

Figure 10:
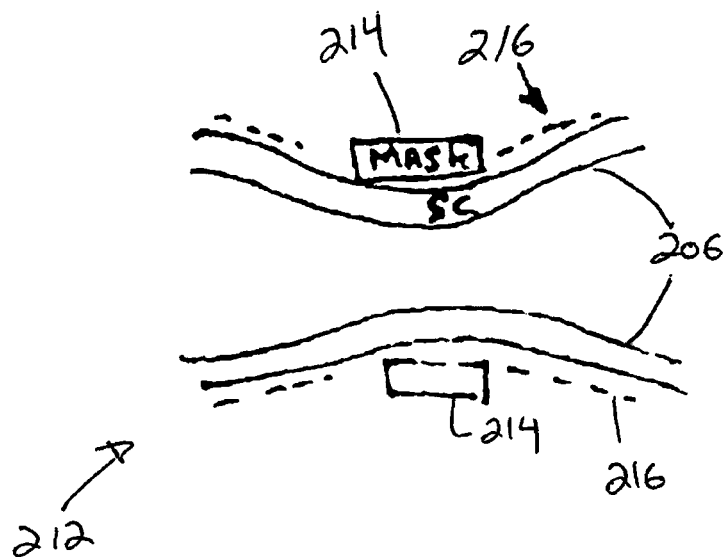

In yet another seen in FIG. 10, a balloon 212 can be created by molding a semi-compliant material 206 into a desired balloon shape. The areas desired to be semi-compliant can be masked or covered with a mask 214 and a thin non-compliant polymer layer 216 can be applied onto the unmasked regions (e.g., the distal region 102A and proximal region 102C of balloon 102). Such noncompliant materials can include polyimide, polyethylene terephthalate, fiber reinforced polymers, and many polymers commonly used for noncompliant balloons. Preferably, the non-compliant polymer 216 can be applied by spray or dip coating and can be further treated to provide crosslinking to enhance the non-compliant properties. Regions of the balloon can be masked during various stages of the process to provide various levels or areas of compliance and noncompliance.

Figure 11:
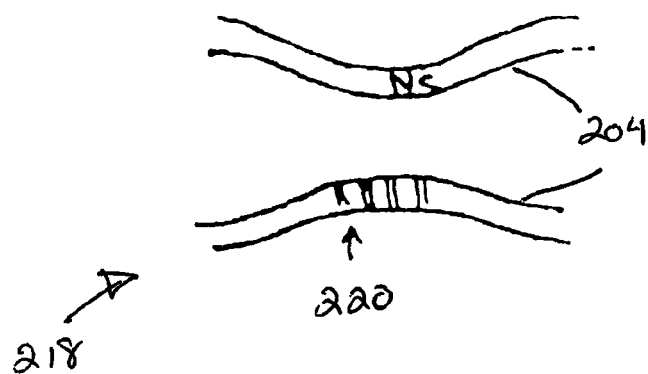

In yet another example seen in FIG. 11, a balloon 218 can be created by molding a non-compliant material 204 into a desired balloon shape. Next, the non-compliant material 204 can be post processed in desired areas (e.g., the area that would become the waist 102B of balloon 102 in FIGS. 1-4) to achieve semi-compliant characteristics. This post processing may include ebeam, chemical treatment or mechanical treatment. In a more specific example, ebeam will reduce crosslinking in most fluoropolymer materials and therefore may increase the compliance in the treated area.

Figure 12:
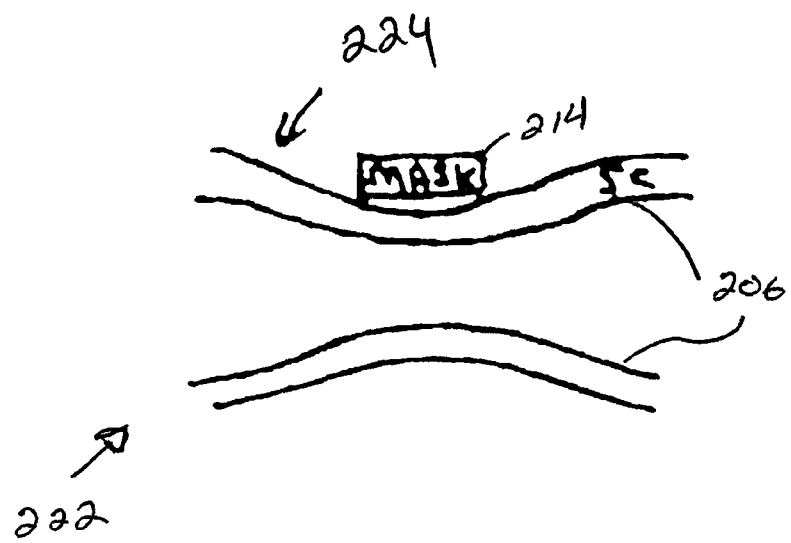

In another example shown FIG. 12, the balloon 222 can be created by molding a semi-compliant material 206 into a desired balloon shape. Next, the semi-compliant material 206 can be post processed in desired areas to achieve non-compliant characteristics. This post processing can include, for example, ebeam to cause crosslinking between most hydrocarbon backbones such as those found in polyethylene. Again, a mask 214 can be used to prevent treatment of areas desired to be semi-compliant.

Figure 13:
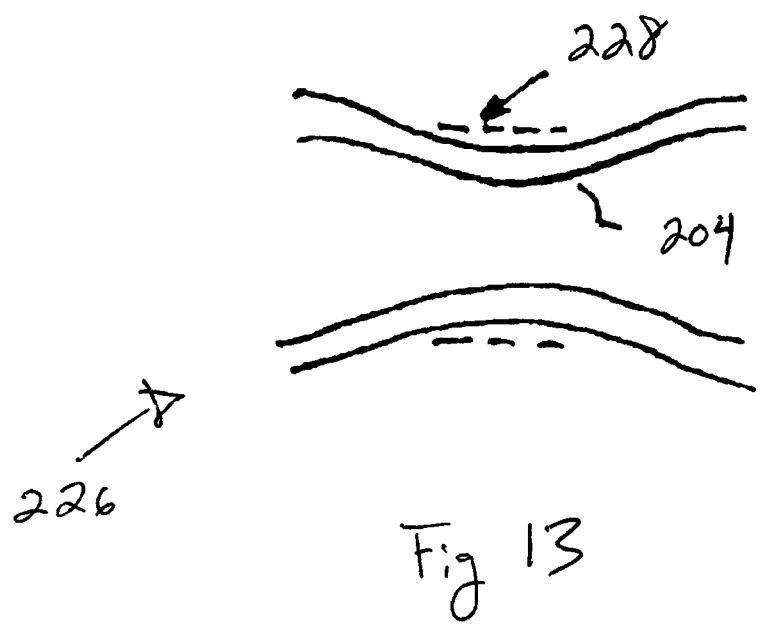

In yet another example seen in FIG. 13, a balloon 226 can be created by molding non-compliant material 204 in a desired balloon shape and placing elastic members 228 around the region that is desired to be semi-compliant shown in FIG. 6. The elastic wrap preferably has a native diameter (i.e., a mostly or partially unstretched diameter) that is smaller than the native diameter of the non-compliant balloon shape. The non-compliant material 204 adjacent and near the elastic wrap 204 may be forced to fold, bend or wrinkle to allow for semi-compliant expansion during use.

In yet another example, a balloon can be created by molding a material with a plurality of circumferential fibers embedded or otherwise located along the axial length of the balloon. By increasing or decreasing the spacing of these fibers, the compliance can be increased or decreased respectively. Additionally, the fibers can be increase or decreased in diameter to further modify the compliance characteristics of the balloon.

Figure 14:
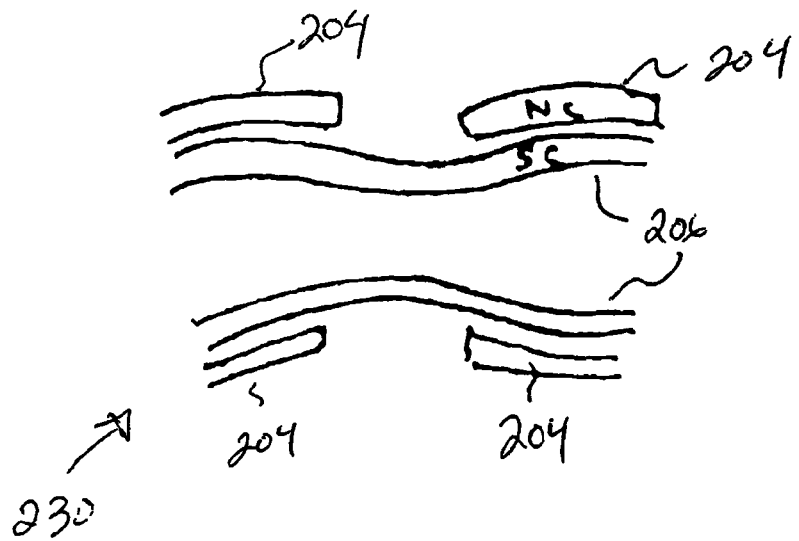

In another example seen in FIG. 14, a balloon 230 can be created by a semi-compliant material 206 that is molded to a balloon shape. A non-compliant material 204 is separately molded to the balloon shape. The distal and proximal portions are cut off of the non-compliant material 204 and placed over the distal and proximal ends respectively of the semi-compliant balloon material 206. Pressure and temperature is applied to the balloon 230 in a mold to fuse the layers together or adhesive or polymer can also be applied between the layers to enhance bonding.

Figure 15:
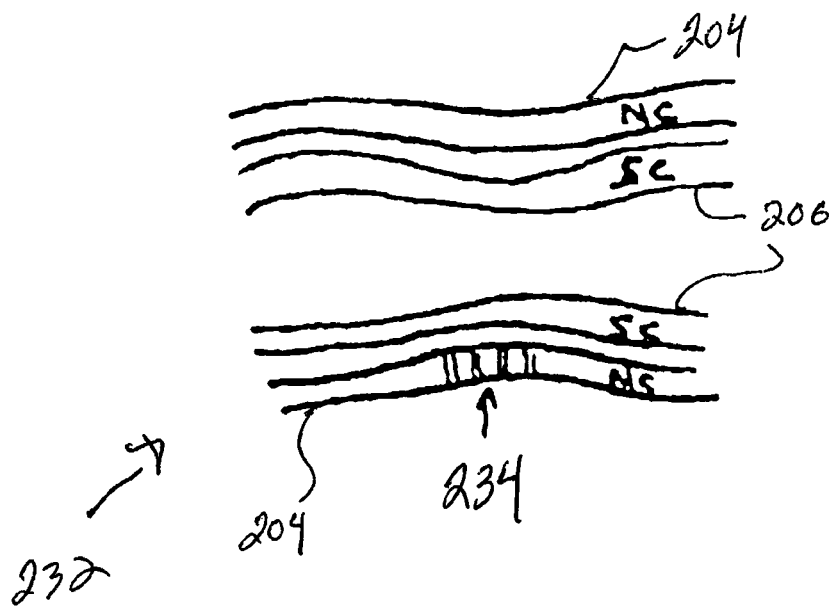

In another example seen in FIG. 15, a balloon 232 can be created by a molding a semi-compliant material 206 and separately molding a non-compliant material 204 into a balloon shape. The middle waist portion of the non-compliant material 204 is weakened to create a more compliant region 234. The non-compliant material 204 is placed over the semi-compliant material 206 and the balloon 232 is placed back in the mold with pressure and heat to fuse the materials 204 and 206 together as previously described. Adhesive or similar bonding material may also or alternately be used between the materials 204 and 206.

Figure 16:
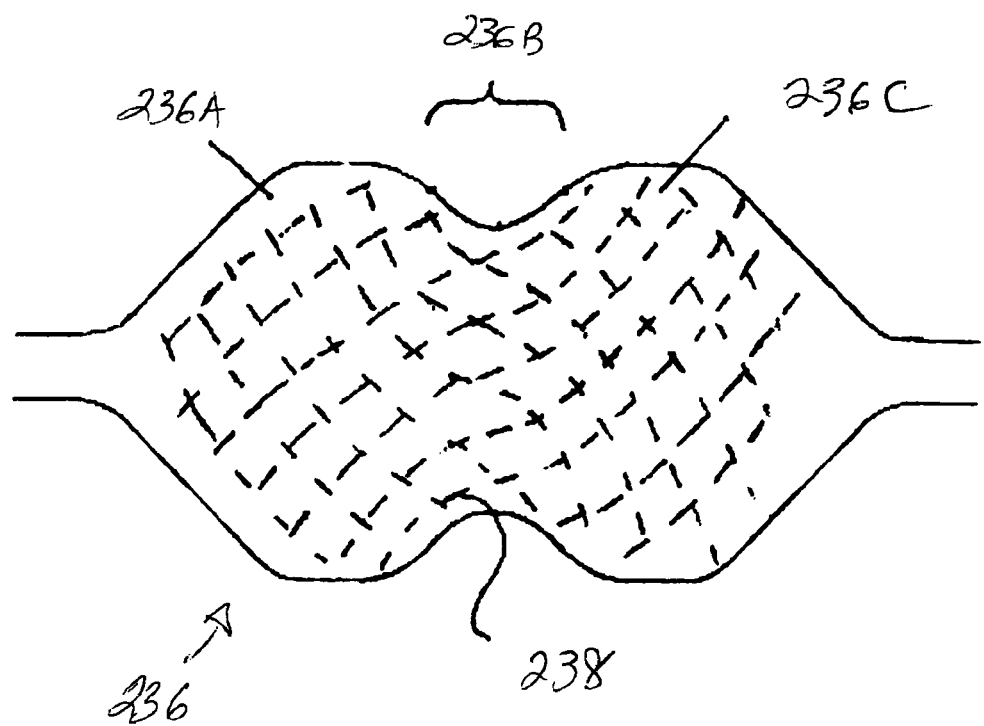
FIG. 16 illustrates a side view of a balloon having a plurality of braided members according to the present invention.

In another embodiment shown in FIG. 16, a balloon 326 is formed with braided members 238 that extends at least through the semi-compliant waist region 236B. The braid can be constructed from multifilament strands of polyethylene terephthalate, polyethylene, or other polymer or thin metal stands. The braid can be bonded to the balloon using UV curable acrylic, polyurethane, or other bonding agent. The braid will allow the waist 236B to enlarge in diameter while causing the waist 236B to reduce in length. This balance will allow the inflection point 133 in the delta pressure/delta volume curve to become more pronounced as contact is made by the waist 236B with the annulus 118. The braided members 238 can also ensure that the waist 236B does not over extend in diameter and cause dissection to the annulus 118. The braided members 238 can also help to hold the non-compliant regions 236A and 236B such that they do not expand in diameter and thereby help to improve the observation of the inflection point 133. The braid angle of the braided members 238 in the waist region 236B may, for example, be more axially oriented than that in the bulbous end regions 236A and 236C of the balloon 236.

Optionally, a third fiber having substantially a circumferential direction and having a diameter approximately equal to an upper limit diameter can be braided into a standard braid that has a fiber angle with respect to the axis of about 42-75 degrees. The presence of the third fiber may limit diameter of the braid such that it cannot extend beyond the upper diameter limit set by the circumferential strand.

In another embodiment, braided member can be bonded over the balloon in its configuration that is not yet expanded. Preferably, this bonding occurs when the waist is expanded to approximately an 18 mm diameter. Here the braid is forced into a smaller diameter by pulling apart on each end of the braid. This smaller diameter portion is then bonded to the waist. Further, the braid is bonded to the larger diameter non-compliant end portions of the balloon.

An alternate method for forming one embodiment of the balloon includes forming a zig-zag shape from a multifilament strand of PET, Dacron, nylon, or other high strength material ranging in diameter from 0.0005-0.003 inch and preferably 0.001-0.002 inch. Each micro fiber of the multifilament strand can be approx. 5-20 microns in diameter. Also nitinol multifilament or monofilament strands of similar dimensions can be used. The zig-zag shape can have an angle from the average axis direction of 30-60 degrees and preferably 40-50 degrees for a diameter change for the waist of 18 to 24 mm as the zig-zag strand becomes straightened under force. The zig-zag strands are formed by placing the generally straight strand along a comb-like fixture that forces the strand between the opening of another the combs-like fixture. Similarly the teeth of a cross cut wood saw can be used as a mold to force the strands into the valleys of another cross cut saw. The strand is then heat treated to form a zig-zag pattern while being held by the fixture or mold.

With the balloon in a smaller diameter configuration, the zig-zag strand is wound around the waist region (preferably inflated to about 18 mm in diameter) in a spiral manner. Note that circles of zig-zag material can also be used. For example a zig-zag can be cut from a tube or nitinol using a laser and placed around the waist of the balloon. The zig-zag strands are then bonded to the waist using an elastomeric adhesive such as silicone, polyurethane, a copolymer of these polymers, and other polymers.

In another embodiment, a dog-bone shaped balloon can be formed by an approximately 25 mm in diameter cylindrical balloon composed of a non-compliant material such as PET or nylon. In the central region of this balloon where the waist is intended to be located, the non-compliant material is folded. This can be done by the initial mold that forms the balloon to begin with such that it has a rippled or corrugated shape running axially in the waist region. Alternately, it can be formed as a post process by placing a metal element inside the balloon from each end opening and a mold outside the balloon and allowing the balloon material to be forced into a rippled or corrugated shape. The corrugated shape will allow the non-compliant balloon to fold in a controlled manner when it is expected to constrict down due to the elastomeric waist material (previously described).

As a second step, an elastomeric waist can be formed that extends from a small diameter of about 18 mm in the center of the waist to a diameter of approx 24 mm at the ends of the waist. This component can be formed from a molding operation or an extrusion operation followed by a post processing method to form or mold the proper shape. The material can be silicone, polyurethane, a copolymer, or other elastomeric polymer.

The non-compliant balloon is then expanded out to its expanded configuration at a lower pressure ranging from 0.1-4 Atm. The waist is then placed over the center of the non-compliant balloon and bonded to the center. Upon release of pressure, the waist portion of the balloon contracts due to the shape and force of the waist portion. Upon expansion to a larger pressure, the non-compliant balloon material located in the waist region ensures that the waist cannot expand beyond 25 mm.

As previously described, the waist 102B of the balloon 102 (FIGS. 1-4) is preferably compliant or semi-compliant, meaning its diameter will differ between the proximal portion 102C and distal portion 102A, depending on the inflation pressure within the balloon 102. In other words, the non-compliant regions will remain relatively constant in diameter during inflation while the semi-compliant regions will grow with more pressure For example, the waist 102B may be 16-20 mm in diameter in its equilibrium state and capable of stretching to engage the annulus at 19-25 mm in diameter whereas the proximal and distal ends remain at a relatively fixed diameter ranging for approximately 23-28 mm.

Preferably, the waist 102B of the balloon 102 is "undersized" in its equilibrium, low pressure, state (i.e., sized smaller relative to the annulus) by about 3-5 mm. For example, if the target annulus 118 of the patient's valve 120 is about 23 mm, a balloon 102 with a waist 102B at equilibrium is about 20 mm. Preferably, this example waist 102B grows by 2 mm at a pressure of 2 ATM to a diameter of 22 mm. At this diameter of 22 mm and an internal pressure of 2 ATM, the outward force exerted upon the annulus is about zero since it takes 2 ATM of pressure just to reach 22 mm in diameter. As this example balloon 102 becomes further pressurized to 3 ATM, its waist 102B grows further to 23 mm and it may come into contact with the wall of the annulus 118, but would likely not exert much, if any pressure on the annulus 118 (since the waist 102B would just begin to engage in contact).

In contrast, the proximal portion 102C and distal portion 102A apply an outward force of about 3 ATM against the leaflets 116 and left ventricle outflow tract 114 since these portions 102A and 102C are non-compliant and are in contact with these structures starting at the equilibrium pressure. If the pressure was further increased to 4 ATM, only 1 ATM of outward force maximum would be applied to the annulus 118. In this example, it is believed that exposure of the annulus 118 to a pressure of 2 ATM, for example, or less will not result in a dissection (i.e., damage). If the actual annulus diameter was 22 mm and the waist came in to contact with the annulus at 2 atm, the annulus could be exposed to 2 ATM of pressure if the internal balloon pressure was 4 ATM.

Further, the waist 102B preferably self-locates such that the waist 118 automatically locates over the annulus 118, thereby avoiding damage to other portions of the valve 120. For example, if the waist 102B of the balloon was located low into the left ventricle outflow tract 114, then the proximal portion 102C, normally located in the sinus 112, may expand in the annulus 114 and possibly cause dissection. If the waist 102B was somehow positioned in the sinus 112, then the inflated waist 102 would not achieve a diameter capable of "cracking" the calcified leaflets 116 at their base. The length of the waist 102B must be adequately sized to the annulus 118 to avoid similar outcomes.

To aide in the self positioning, the outside of the balloon 102 can be slippery so as to enhance its ability to "slide" into a desired position with the waist 102 positioned over the annulus 118. Alternately, the outer surface of the balloon can be textured or roughened to help hold the balloon into position during the inflation.

Note that the term non-compliant, which has been used in this specification, refers to material that is relatively inelastic. In other words, such material has little or no stretch under most, intended circumstances, such as application of moderate pressure. The terms compliant or semi-compliant, which have been used in this specification, refer to material that includes at least some elasticity. In other words, such material will stretch with little or no damage to the material under most, intended circumstances, such as application of moderate pressure. The waist material should preferably also be resilient such that it returns to its initial diameter when the pressure is reduced.

The specific balloon description presented below is an example of one balloon size that is intended to cover a size range of annulus diameters from 21 to 24 mm. It is a dog-bone shaped balloon with a waist that is semi-compliant and non-compliant bulbous end-regions. For the purposes of this specific example, FIG. 1 will be further referred to.

The balloon 102 has a length 111 of between about 40-80 mm and preferably 50-70 mm. Regions 102A and 102C are non-compliant while region 102B is semi-compliant. The balloon 102 has a working pressure of between about 4-5 atm; a burst pressure between about 6-7 atm with the tear direction preferably in the axial direction. The wrap profile of the balloon 102 is about 10-12 Fr and the catheter shaft 104 is preferably between about 9-12 Fr. The guidewire lumen is configured for over the wire techniques with about a 0.036" wire. The balloon waist 102B has a length 109 when of about 5-10 mm axial length at 0.1 ATM and about an 18-21 mm maximum diameter 105 in its center. Preferably, each section 102C and 102A have a maximum diameter 103 and 107 of between about 25-56 mm.

The following are example measurements of the balloon waist 102B at various pressures:

| Balloon Pressure | Diameter |
| --- | --- |
| 0-0.1 ATM | 18 |
| 1 ATM | 19.5 |
| 2 ATM | 21 |
| 3 ATM | 22.5 |
| 4 ATM | 24 |

Preferably, two circumferential Angiographic marker bands are located on the surface of the balloon 102 and optionally on the central shaft 104, within the balloon and near the waist area 102B. Such marker bands can be a ring of radioopaque material swaged or bonded onto the catheter shaft or applied via vapor deposition or coating process onto the outside of the balloon Balloon ends can be formed at 4 mm OD at each end. One example places approximately a 0.038 in ID×0.046 in OD tubing through the catheter shaft and through the balloon to provide passage for a 0.035 inch guidewire. The distal end of the balloon is bonded to the guidewire tubing. Some expansion in the length of the balloon may occur under pressure due to expansion of the waist. It may be desirable to reduce any balloon curving that occurs as the balloon is expanded under pressure by preferably using a guidewire tubing with similar axial expansion as the balloon.

In the previous example, the waist is suggested to undergo an expansion from about 18 mm to 24 mm as the pressure increases from a small pressure above zero ATM (i.e., 0.1 ATM) to 4 ATM. This waist compliance is described as a linear compliance. However, since most elastomeric polymers are not linear, it is desirable that the middle of the waist achieves the diameters indicated in the example at the two points which occur at 2 ATM and 4 ATM. These two middle waist diameters are 21 mm and 24 mm at 2 ATM and 4 ATM, respectively. Preferably, the diameter of the middle of the waist is smaller than 18 mm in its natural state (i.e., at approx zero pressure) in order achieve the 21 mm and 24 mm data points.

In some examples, the semi-compliant waist is joined to non-compliant bulbous ends. This junction of a semi-compliant material with a non-compliant material can generate a discontinuity that may result in breakage. A small transition region may reduce this breakage although it should be noted that such a transition may not be appropriate for all balloon materials and designs. If a transition region is necessary, then the transition region can be formed in the waist, thereby making the axial length of the waist somewhat smaller than the 5 mm-10 axial length listed on the drawing.

The non-compliant bulbous regions 102C and 102A are intended to maintain a fixed diameter from 1 ATM to 4 ATM. If the non-compliant regions stretch with an increase in pressure, it may be difficult to detect the stretching waist by monitoring the balloon pressure. Therefore the bulbous regions should preferably be made of a material that resists any circumferential stretching.

As discussed in U.S. Publication No. 2005/0090846, the contents of which have been previously incorporated by reference in this application, an alternate embodiment of a balloon is possible according to the present invention, including a non-compliant waist and semi-compliant proximal and distal portions. In one example, the balloon can have the characteristics described below, although it is recognized that this balloon embodiment may not have the ability to measure the annulus in a manner described for the semi-compliant waist balloon of FIGS. 1-4.

The balloon includes a waist that is non-compliant and at least one end portion that is semi-compliant. However, both end regions may also be semi-compliant. The end portions are able to expand under pressure thereby allowing the bulbous proximal portion to push the leaflets back to an amount that is dependent upon the internal balloon pressure, while the waist cannot over-distend the annulus.

An internal pressure of approx 2 atm can cause the proximal portion of the balloon to expand outwards by approximately 10-20% beyond its equilibrium size causing the diameter of the balloon to extend from approx 20 mm to 24 mm. The balloon can be constructed such that the balloon shape is bulbous in a manner described earlier where the waist is smaller than the bulbous regions by approximately 15-25%. Alternately, the balloon can be almost cylindrical in shape with the waist only approximately 10% smaller than the bulbous ends at a pressure of 1.5 atm. The waist can range in length from 1-10 mm.

The balloon can be constructed by applying a non-compliant material, a spiral wrap, a braid, or woven fabric in the waist region of a semi-compliant balloon to make the waist into a non-compliant region. Balloon strengthening can alternately be applied to the waist via chemical or other means of crosslinking.

In anther alternate embodiment, the entire balloon may be composed of non-compliant material. A dog-bone shaped balloon with a non-compliant waist approach may require a close estimate of the annular diameter within 1 mm and therefore the balloon waist should be sized to match this diameter. In one example, a dog-bone shaped balloon is created such that it is entirely non-compliant and provides the balloon sizes in increments of 1 mm annular diameter size variations.

This all non-compliant balloon operates at a pressure ranging from 3 atm to very high pressures of over 10 atm. Safety is obtained by ensuring that the waist does not grow. Preferably, the dog-bone shaped balloon is slippery so that it moves to self-center the waist at the annulus 118. Failure to self center may result in the larger portions of the balloon being positioned at the annulus and thereby causing the annulus to dissect.

In another embodiment, a dog-bone shaped balloon is entirely semi-compliant. Hence, this balloon configuration does not constrict the growth of the bulbous end regions of the balloon. The change in the pressure/volume curve that is observed when the waist comes into contact with the annulus is not as obvious as with other described embodiments since the end bulbous regions are still able to grow in volume as the pressure inside the balloon is increased.

One difference from the previously described, all non-compliant balloon is that a compliance curve may be used to size the diameter of the annulus. Following contact of the waist with the annulus, the annulus could increase in diameter due to an increased operating pressure but the waist would be sized accordingly such that annular expansion would not be significant. The sinus and distal portion of the balloon would continue to increase proportionally with increasing pressure. The diameter that is selected for the balloon waist would be set by a diameter that would not stress the annulus. If the material for this semi-compliant balloon were such that generally higher pressures were being used during the inflation and prior to contact of the waist with the annulus (i.e., greater than 2-5 atm), then the entire balloon could be made of the same semi-compliant structure. The internal pressure within the balloon would impart very little force to the annulus. The safety is gained by ensuring that the annular diameter is larger than the waist during leaflet expansion and inflation is terminated soon after contact of the waist with the annulus. Some operating challenges with the totally semi-compliant balloon can occur due to continued expansion of the bulbous portions of the balloon after that waist makes contact with the annulus, thereby reducing the magnitude of the slope change in the pressure versus volume curve after the inflection point.

In a manner similar to the previously described, all non-compliant balloon, the balloon may be slippery to ensure that it self centered on the annulus. If it did not self center, one could easily cause an annular dissection due to placement of the proximal or distal portions of the balloon in the annulus region. This higher pressure semi-compliant balloon may be manufactured out of nylon or other semi-compliant material or it may use a composite wall structure having a braid or other fiber matrix bonded to or contained within the balloon wall, if the profile was not a limiting factor.

Figure 17:
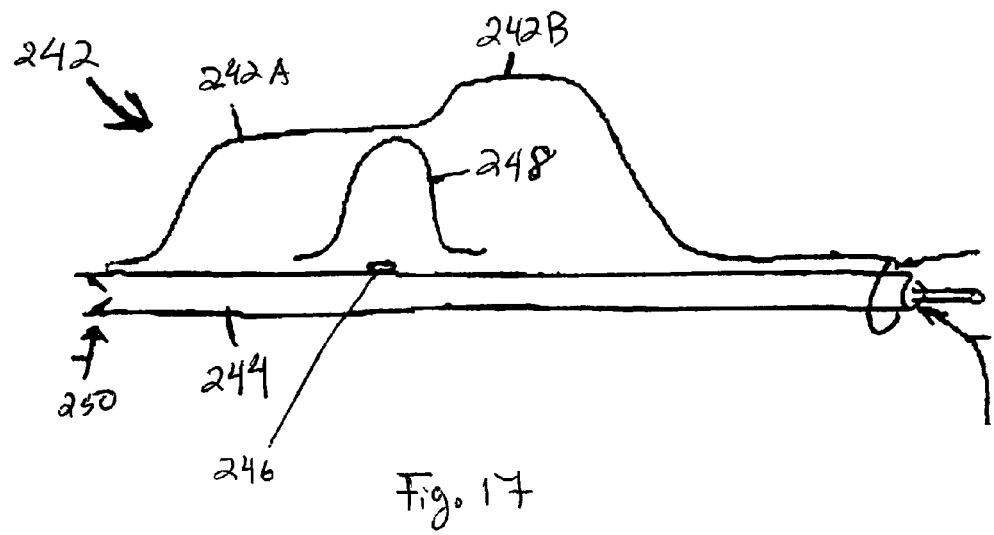
FIGS. 17 and 18 illustrates a side view of a dual balloon catheter according to the present invention.
Figure 18:
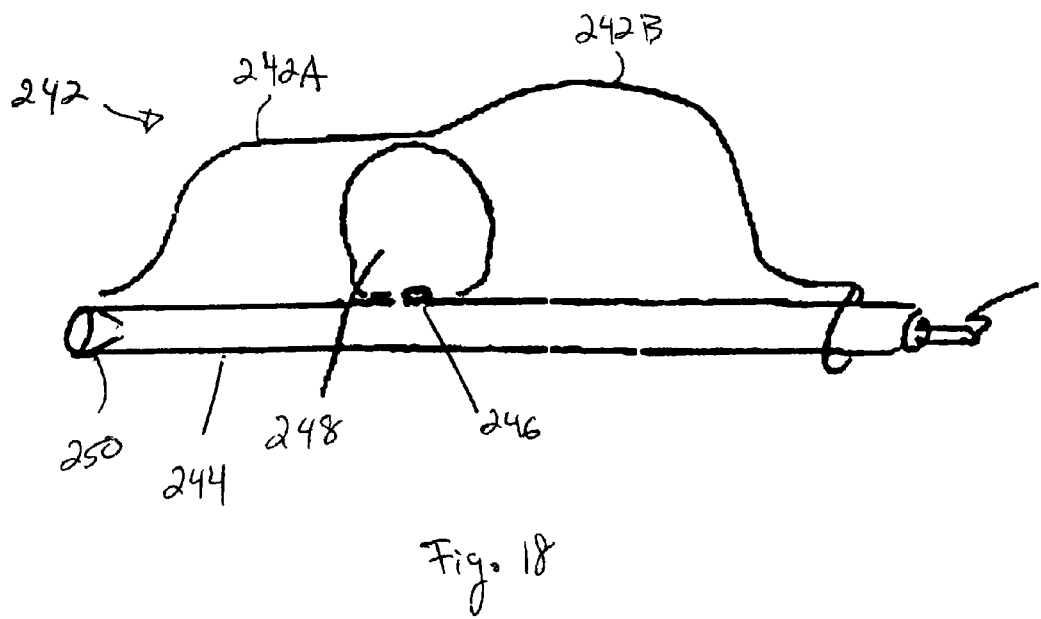
Figure 19:
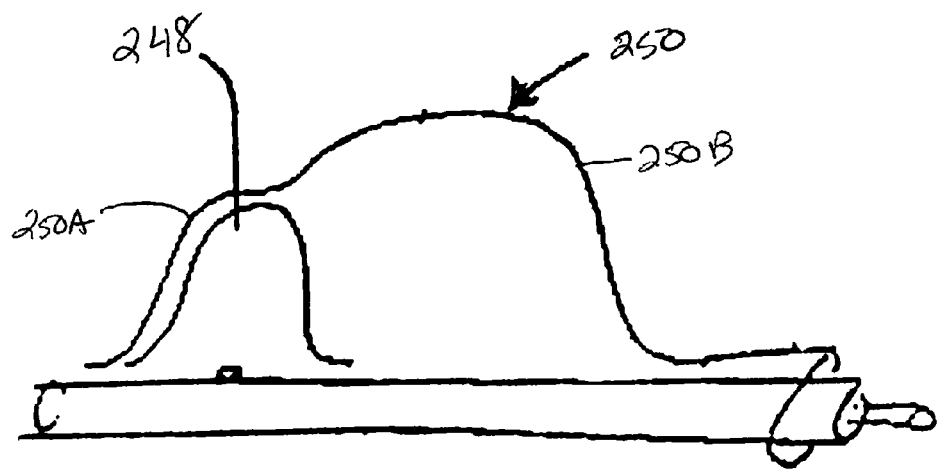
FIG. 19 illustrates a side view of dual balloon catheter according to the present invention.

FIGS. 17 and 18 illustrate another embodiment of a valvuloplasty balloon 242 according to the present invention. This balloon 242 includes a larger diameter region 242B for expanding against valve leaflets and a smaller diameter region 242A for anchoring in the left ventricle outflow tract. The size of the patient's annulus can be measured by a smaller inner balloon 248 that is located over an inflation port 248 on the catheter shaft 244 and located within the balloon 242.

The inner balloon 248 has an inner balloon inflation lumen that connects to port 246, allowing the inner balloon 248 to be inflated first and serve as a positioning balloon that locates this balloon upstream and adjacent to the aortic annulus. The inner balloon can be bonded to the shaft to obtain a shape or profile that best allows positioning of the balloon. Once this balloon is in place, the larger outer balloon can be inflated using a separate outer balloon inflation lumen to dilate the leaflets via the sinus portion of the outer balloon 242.

Figure 20:
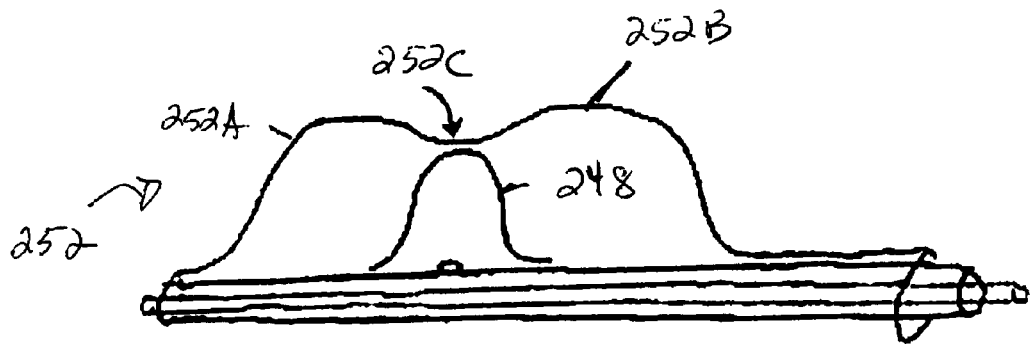
FIG. 20 illustrates a side view of a dual balloon catheter according to the present invention.

This sinus portion 242B of the outer balloon has a larger diameter than the locator balloon 248 and is sized to push the aortic leaflets outward into the aortic sinus. The outer balloon can have a distal shape that is cylindrical as seen in FIGS. 17 and 18, a balloon 250 with proximal end 250B and a distal end 250A that follows the inner balloon 248, or a balloon 252 having a bulbous proximal end 252B and a bulbous distal LVOT portion 252A that forms a waist region 252C as seen in FIG. 20.

The outer balloon of the embodiments of FIGS. 17-20 can be constructed using any of the construction means described in the previous embodiments including non-compliant, semi-compliant or a combination of both materials. The outer balloon can, for example, have a semi-compliant waist and be used to measure the annular diameter as described earlier.

The inner balloon can be constructed of either semi-compliant or non-compliant materials. The inner balloon can also be used to assess the diameter of the annulus by monitoring its volume and calculating the diameter of the annulus as previously described in this specification. Pressure measurements made in either the inner balloon or between the inner and outer balloon can also be used as described earlier to monitor change in pressure versus change in volume to identify that contact has been made with the annulus. Various sensors such as ultrasound, piezoelectric, electrical resistance and others can be used along with this embodiment as described in previous embodiments to measure the annulus diameter.

It should be understood that drugs may be applied the outside of any of the previously described embodiments for treatment purposes. For example, drugs similar to the "olimus" or "paclitaxel" groups may be used to offset the local deposit of calcium and possibly alter osteoblast calcium deposition.

It is also possible to configure the shape of the balloon 102 to allow perfusion during the procedure. For example, perfusion channels or passages may be included in the balloon 102.

Figure 21:
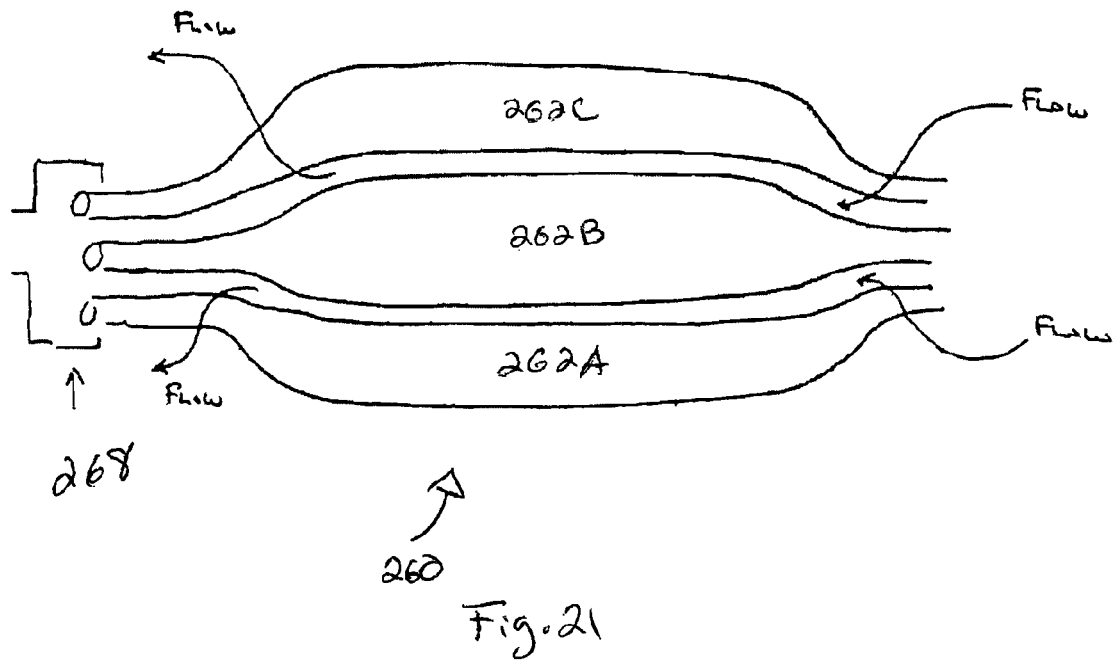
FIG. 21 illustrates a side view of a multi-balloon catheter according to the present invention.
Figure 22:
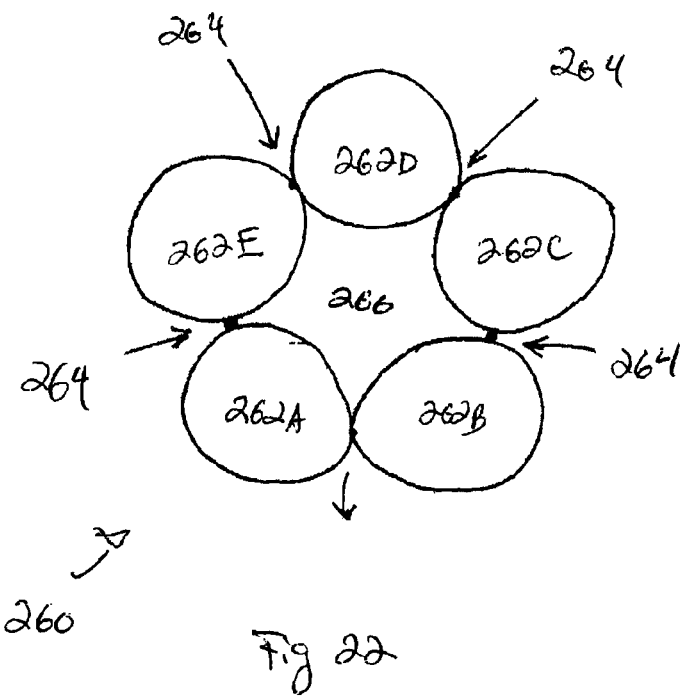
FIG. 22 illustrates a cross sectional view of the multi-balloon catheter of FIG. 21.

FIGS. 21 and 22 illustrate a perfusion balloon device 260 that includes 5 individual balloons 262A-E or 5 balloon compartments arranged in a pentagon shape around a flow area 266. Each of the balloons 262A-E are attached to each other at attachment sites 264. Each balloon 262 provides support to the central flow area 266 by intimate contact with two other balloons 262. The central flow area 266 for the 5 balloons 262 is preferably about 0.48 cm sq, which is though to be enough to maintain adequate perfusion to the brain while the balloons 262 are inflated. Fewer balloons can also be used however this results in a smaller central flow area. If 3 balloons are used, the area is preferably about 0.056 cm sq and for four balloons it is preferably about 0.237 cm sq. The shape is more stable with fewer balloons however the flow area is much less. If more than 5 balloons 262 are used, the flow area may be increased, however the stability of the shape may be reduced.

Each balloon 262 is attached to a central manifold 268 at the proximal end of the balloons 262 such that all of the balloons 262 are inflated simultaneously. The flow of blood is provided via access between the balloons 262 at the distal end and flows down the central flow area 266 and passes between the balloons 262 at the proximal end. It is noted that the 5 balloons 262 can be formed such that the balloon inlets are located off to one side of the assembly rather than located on the central axis of the assembly as shown. Locating the inflation inlet and manifold off of the central axis would potentially allow for a more direct flow path for the blood into and out of the assembly.

Figure 23:
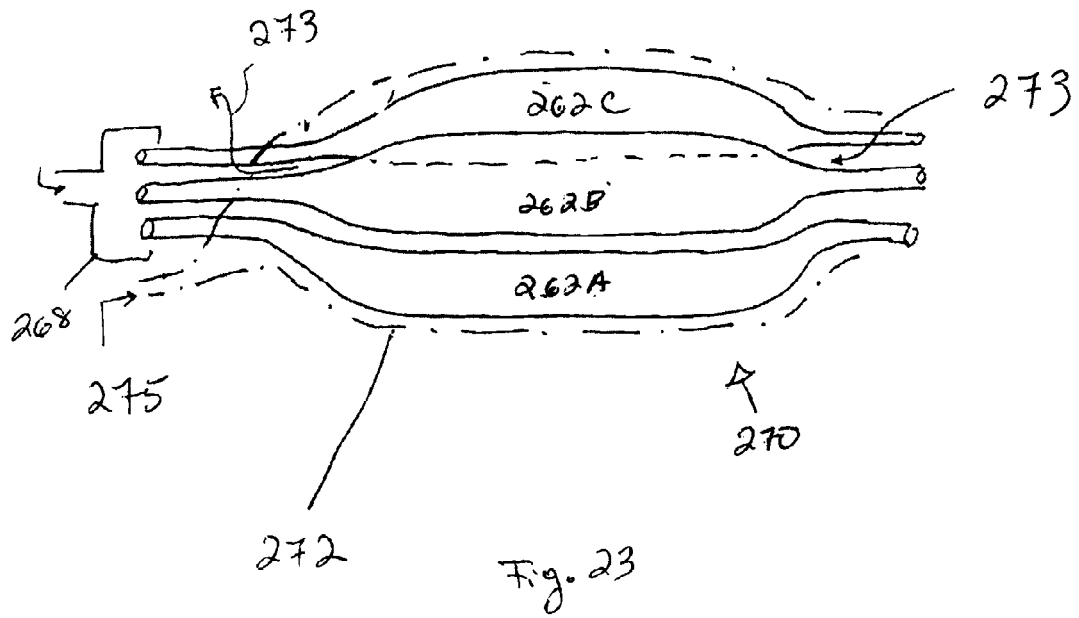
FIG. 23 illustrates a side view of a multi-balloon catheter according to the present invention.
Figure 24:
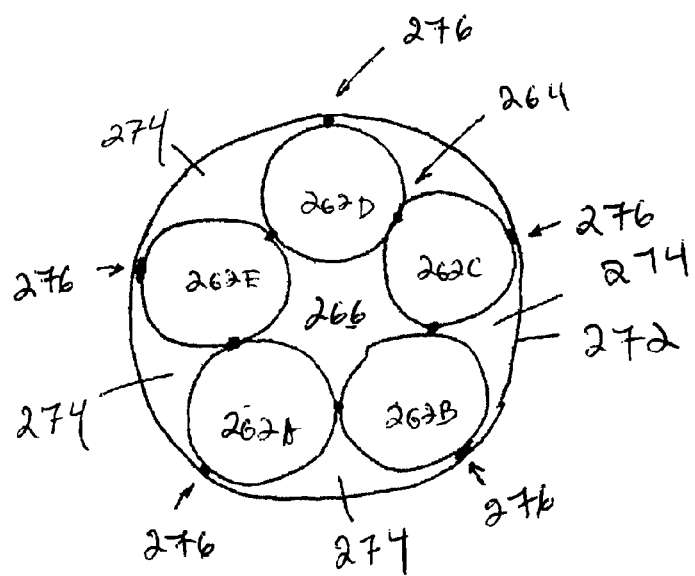
FIG. 24 illustrates a cross sectional view of the multi-balloon catheter of FIG. 23.

FIGS. 23 and 24 illustrate a balloon valvuloplasty device 270 which is similar to the previously described device 260 except for the addition of an external wrap 272 around the outside of the 5 balloons 262. The external wrap 277 is a thin but strong plastic material that also serves as a balloon around the outside of the five balloons 272. The external wrap 272 can also be preferably attached to the 5 balloons 262 at attachment sites 276. Flow of fluid such as blood can occur through the central region 273 located between the five balloons 262.

The attachment of the balloons 262 to the external wrap 272 not only provides stability to the shape of this balloon assembly 270 but also allows inflation to occur between each of the balloons on the outside of the balloons in external spaces labeled 274 via a separate inlet lumen 275 to the external space. Expansion of the external space 274 at an external wrap pressure allows the entire structure to provide expansion to external tissue forming a round or continuous shape. It is believed that the external wrap pressure should be somewhat lower than the balloon inflation pressure such that the balloons are providing an even support to this external wrap. The pressure in the external wrap preferably ranges between 1 and 6 ATM and preferably between 2 and 5 ATM. The pressure in the 5 balloons may range from 2 to 20 ATM.

A seal must be made between the external wrap and each of the individual balloons 262 separating it from the flow area 266 for the perfused blood through the central flow area 266 of the balloon assembly 270. This flow passage must be provided at the proximal and distal end of the balloon assembly 270 and includes an attachment with each of the 5 balloons 262. A continuous passage for blood is formed from the central flow area 266 through a space located between at least two balloons that are themselves sealed independently to the outer wrap in the proximal and distal ends of the balloon assembly.

Figure 25:
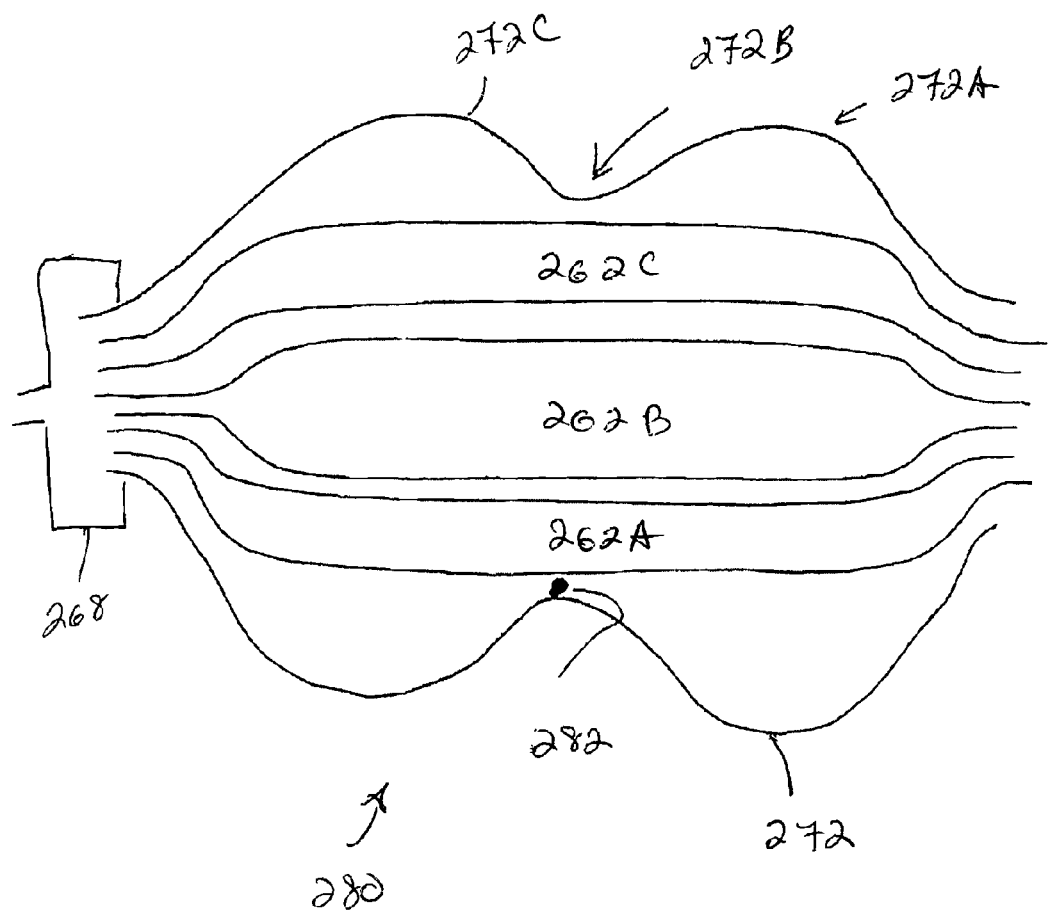
FIG. 25 illustrates a side view of a multi-balloon catheter according to the present invention.

FIG. 25 illustrates a balloon 280 similar to previously described balloon 270 formed from the 5 individual balloons 262 but further having an external wrap 272 that has a dumbbell or lobular shape. A proximal bulbous region 272C provides expansion to the sinus region and the distal bulb 272A provides positioning support to the balloon assembly such that it does not move axially and instead tends to self-center with the balloon waist 272B located at the annulus of the aortic root. The functionality of the balloon assembly 280 is similar to that described in FIGS. 1-4. To enhance the overall shape, the waist region 272B can be attached to each of the balloons at attachment points 282.

Figure 26:
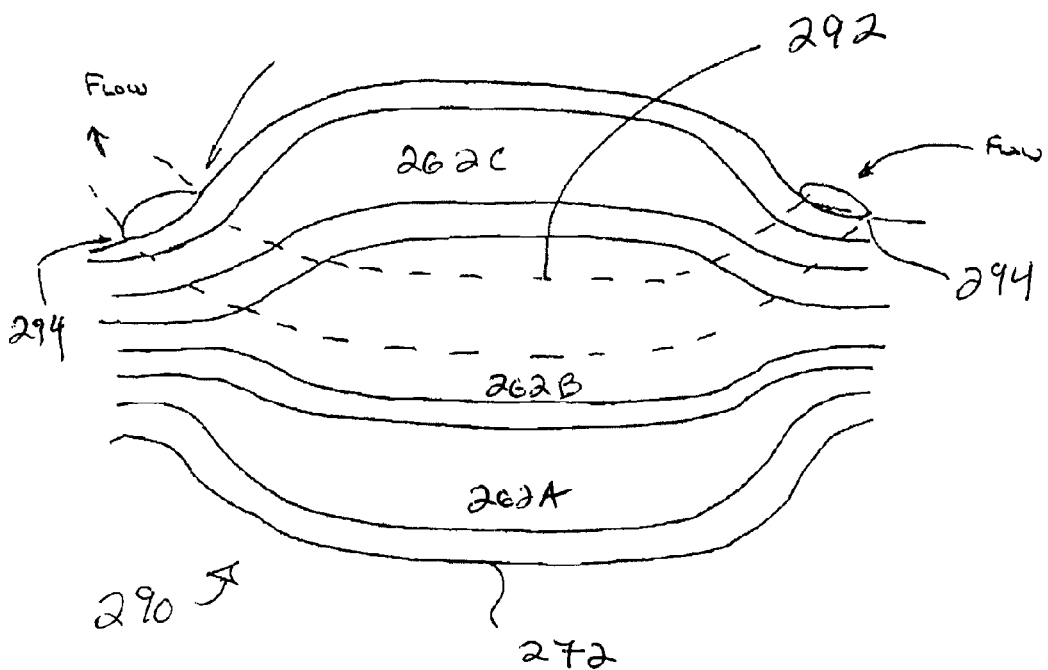
FIG. 26 illustrates a side view of a multi-balloon catheter according to the present invention.
Figure 27:
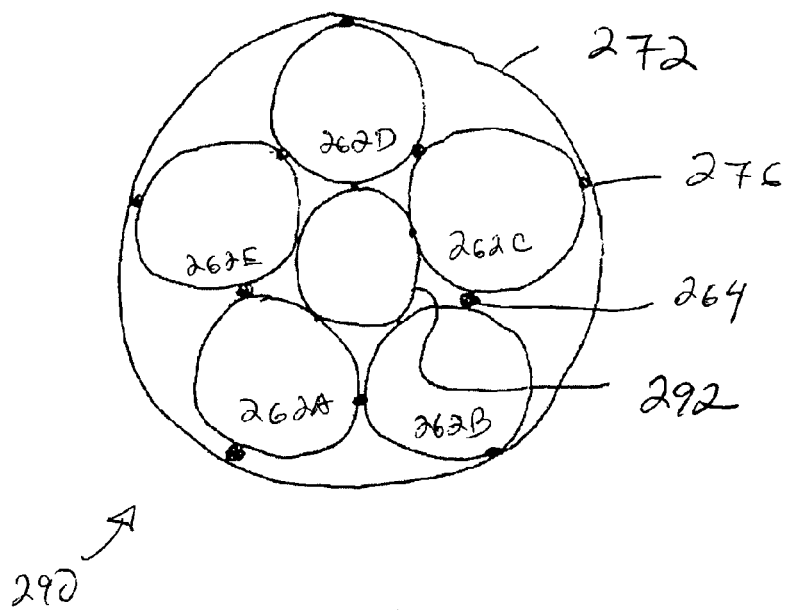
FIG. 27 illustrates a cross sectional view of the multi-balloon catheter of FIG. 26.

FIGS. 26 and 27 illustrates a valvuloplasty balloon device 290 that is similar to the previously described device 270, but with an additional wrap or tube that forms a passage 292 within the balloon assembly 290. The internal passage 292 provides a confined flow space for the blood through the central portion of the balloon assembly 290. The internal passage 292 allow for passage of blood from the central flow area through the external wrap 272 and allows the external wrap 272 to form a continuous space separate from the flow area for the blood. The internal passage 292 forms a seal 294 with the external wrap at the proximal and distal ends of the balloon assembly.

The perfusion balloons described in FIGS. 21-27 can be formed from 5 separate balloons positioned adjacent to each other and having an external wrap placed around it. The manifolding of the inflation fluid can be accomplished in a variety of ways one of which was shown in FIG. 21. It is also possible to form the balloon assembly and accomplish the manifolding of fluid in other ways.

Five balloons can be positioned adjacent to each other as described earlier with openings directly between balloons to allow inflation fluid to access from one balloon to another. Such openings can connect the balloons, thus allowing manifolding of the inflation fluid to each of the five balloons. The ends of the balloons can be flattened or folded and sealed.

Figure 28:
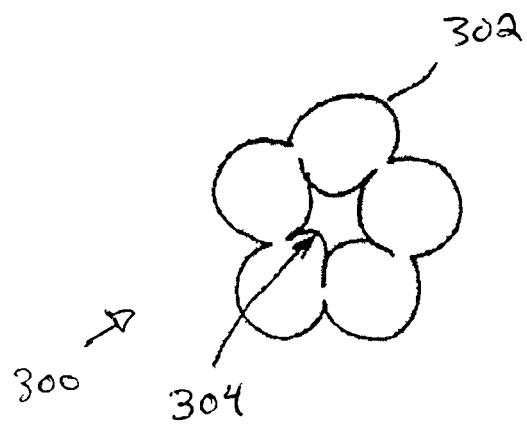
FIG. 28 illustrates a cross sectional view of a multi-chamber balloon catheter according to the present invention; and, FIG. 29 illustrates a cross sectional view of a multi-chamber balloon of FIG. 28 in a molding chamber.

The balloon assembly having multiple balloon-type cylindrical shapes located adjacent to each other can be formed from two cylindrical tubes that form the inner half and outer half of the multiple cylindrical shapes. One can form the balloon assembly 300 having five internal cylindrical balloons and an outer wrap from three cylindrical balloons as shown in FIG. 28. The outer balloon half 302 is a thin walled cylindrical tube; its perimeter is equal to the additive perimeters of the outer halves of each of the five balloon-type cylindrical shapes adjacent to each other. The inner balloon half 304 is somewhat smaller than the outer balloon half and is used to form the inner halves of each of the five balloon cylindrical shapes.

Figure 29:
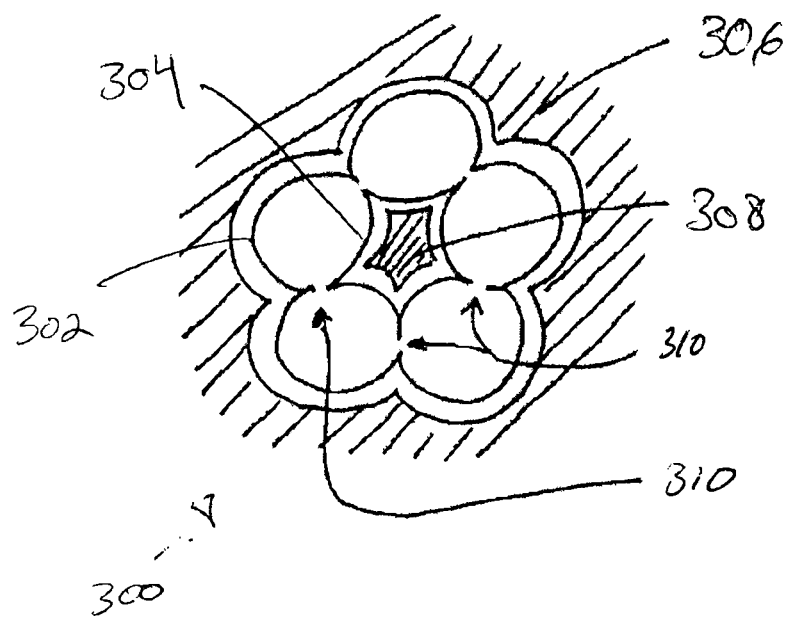

FIG. 28 further shows how the inner 304 and outer balloon halves 302 are positioned to effectively form five adjacent balloon-type cylindrical shapes. An inner forming tool 308 and an outer forming tool 306 are placed as shown in FIG. 29. Heat or other bonding method is used to attach the inner and outer balloon halves 302 and 304 together at the inner/outer attachment points or surfaces. In the region of balloon contact where an opening 310 is needed to provide passage for inflation fluid, a surface contact seal can be formed such that a leak free opening can be made within this seal from one compartment to an adjacent compartment.

An external wrap can be sealed around the outer balloon half as described earlier.

The external wrap can have a cylindrical shape or a bilobular or dumbbell shape as appropriate to its various applications including valvuoloplasty. The material can be noncompliant, semicompliant, or a combination of noncompliant and semi-compliant. In one embodiment the waist region is formed from a semicompliant material and each of the bulbous regions can be noncompliant. Alternately, the entire outer wrap can be formed from either a noncompliant or a semicompliant material.

The perfusion balloons described above allow dilatation of the aortic valve leaflets for a longer period of time while allowing blood to flow within the internal flow area. The increased time of dilation may allow the leaflets to undergo viscoelastic creep and create fractures within the tissue that allows the flow area for the valve to be greater than without the benefit of a longer inflation time. The increased flow area may allow for a greater durability for a valvuloplasty procedure.

The benefit of providing for perfusion during a valvuloplasty procedure may also enable other therapeutic benefits that are not normally viable with the standard valvuloplasty procedure that only allows balloon inflation for a period of 10-15 seconds. For example, cryoplasty has been very successful for treatment of atherosclerotic disease in the leg. Application of cryo therapy with the balloon assembly presented herein may allow the valve leaflets to undergo crystalline formation that can lead to enhanced leaflet fracturing or remodeling that can provide for potentially greater durability. Cryo fluid can be introduced into the individual balloons or into the external space to provide the standard Joule-Kelvin effect that is used in other standard cryo systems. Alternately, application of a restenotic drug to the surface of the leaflets may be enabled by allowing the application to occur over a longer period of time.

Ultrasound may also be used with the previously described perfusion balloons. More specifically, an ultrasound transducer or multiple transducers can be located in the external spaces around the perimeter and within the external wrap of the perfusion balloon. Alternately ultrasound transducers can be located within each of the cylindrical balloons or located in either of the fluid lines in fluid communication with the interior of the balloons or the external spaces around the balloons. For example, an axially vibrating sheathed wire can be located in the fluid channel that is used to inflate the five distally located balloons. The means to vibrate the wire can be located outside of the body and can be a part of the manifold of the catheter. The vibrating motion then is transmitted via the wire down the catheter shaft and is seen as a small pressure pulse within the fluid of the balloons that occurs very rapidly at a frequency typically used to break up plaque or calcium; this frequency could be in the ultrasound range. As the perfusion balloon is inflated, the ultrasound energy located in the fluid of the balloons or the external spaces is activated and causes the calcium within the leaflets to become disrupted resulting in a softer leaflet that tends to remain patent for a longer period of time. Also the leaflets can be broken apart along their commissures more completely resulting in an improved valvuloplasty procedure.

Providing perfusion while undergoing valvuloplasty may require that the balloon assembly be equipped with a temporary valve. Such a valve may consist of, for example, two thin plastic sheets attached along the perimeter of the flow area in much the same way that a venous valve is constructed or it can have a structure similar to a tricuspid valve. The temporary valve can function for periods of minutes or hours if necessary to ensure that blood that is pumped into the aorta does not regurgitate back into the left ventricle. The temporary valve can be placed at either the distal end or the proximal end of the central flow area.

It is further understood that this perfusion balloon assembly can be applied not only to the aortic region for valvuloplasty, but also has application in the venous system, smaller vessels of the body, and other non-vascular tubes of the body. For example, the smaller arterial vessels of cardiovascular system including the carotid artery may benefit from a perfusion balloon. The design of the balloon assembly is essentially the same as that described with a downsizing or upsizing of the balloons to match the vessel diameter of interest.

The present invention has been described above with reference to specific embodiments. However, other embodiments than the above described are equally possible within the scope of the invention. Different method steps than those described above, performing the method by hardware or software, may be provided within the scope of the invention. The different features and steps of the invention may be combined in other combinations than those described. The scope of the invention is only limited by the appended patent claims.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A method comprising:
   providing a pressure system connectable to a catheter for fluid communication with a balloon disposed on a distal end of said catheter;
   dilating valve leaflets with a first region of said balloon;
   subsequent to said dilating said valve leaflets, expanding a second region of said balloon into contact with a valve annulus;
   said pressure system determining contact between said second region of said balloon and said valve annulus;
   wherein said first region of said balloon has a first diameter that is larger than a second diameter of said second region during said contact with said valve annulus.

2. The method of claim 1, wherein said second diameter is measured via fluoroscopy, ultrasound or electromagnetic energy.

3. The method of claim 1, wherein said balloon has a waist having a generally smaller diameter than a proximal and distal ends of said balloon during said dilating said valve leaflets.

4. The method of claim 1, wherein said pressure system further monitors a change in volume.

5. The method of claim 1, wherein said pressure system monitors a change in pressure and a change in volume within said balloon.

6. A method comprising:
   providing a catheter;
   providing a balloon having a first region and a second region, and being disposed on said catheter;
   providing a pressure system communicable with an interior of said balloon; said pressure system:
   expanding said first region of said balloon to achieve a diameter larger than said second region and to dilate valve leaflets;
   monitoring a change in pressure within said balloon;
   subsequent to said expanding said first region of said balloon, expanding said second region of said balloon into contact with a valve annulus;
   determining with said pressure system when said second region of said balloon contacts said valve annulus; and,
   at said contact with said valve annulus, said first region having a first diameter larger than a second diameter of said second region.

7. The method of claim 6, wherein said first region of said balloon comprises noncompliant material and said second region of said balloon comprises semi-compliant material.

8. The method of claim 7, wherein said second diameter is measured via fluoroscopy, ultrasound or electromagnetic energy.

9. The method of claim 8, wherein said balloon has a waist having a generally smaller diameter than a proximal and distal ends of said balloon during said expanding said first region of said balloon.

10. The method of claim 6, further comprising monitoring a change in volume in said balloon.

11. The method of claim 6, further comprising monitoring a change in volume within said balloon and determining said diameter of said second region.

12. The method of claim 6, further comprising determining said diameter of said second region based on determining contact between said second region of said balloon and said valve annulus.

13. The method of claim 6, wherein said first region of said balloon comprises noncompliant material and said second region of said balloon comprises semicompliant material.

14. A method for dilating a valve, the method comprising:
providing a balloon catheter having a balloon and being connectable to a fluid delivery device for inflating the balloon;
advancing the balloon catheter to the valve;
dilating leaflets of the valve to a larger diameter with a non-compliant region of the balloon;
expanding a semi-compliant region of the balloon subsequent to the dilating leaflets of the valve;
monitoring with a pressure system for contact between the semi-compliant region of the balloon with an annulus of the valve.

15. The method of claim 14, wherein said noncompliant region of said balloon is located proximally to said semicompliant region of said balloon.

16. The method of claim 15, wherein said semicompliant region of said balloon has a smaller diameter than said non-compliant region of said balloon during said dilating said leaflets.

17. The method of claim 15, wherein said balloon has a waist having a generally smaller diameter than a proximal and distal ends of said balloon during said dilating said leaflets of said valve.

18. The method of claim 15, further comprising monitoring a change in volume in said balloon.

19. The method of claim 15, further comprising monitoring a change in pressure and a change in volume within said balloon.

20. The method of claim 15, further comprising determining a diameter of said second region based on said monitoring for contact between said second region of said balloon with an annulus of said valve.

21. The method of claim 14, further comprising determining a diameter of said semi-compliant region based on said pressure system determining contact between said semi-compliant region of said balloon and said annulus of said valve.

22. The method of claim 21, wherein said diameter of said semi-compliant region is further determined by monitoring a change in pressure within said balloon.

* * * * *